US011967436B2

(12) United States Patent
Hernandez et al.

(10) Patent No.: US 11,967,436 B2
(45) Date of Patent: Apr. 23, 2024

(54) METHODS AND APPARATUS FOR MAKING BIOLOGICAL PREDICTIONS USING A TRAINED MULTI-MODAL STATISTICAL MODEL

(71) Applicant: Quantum-Si Incorporated, Guilford, CT (US)

(72) Inventors: Marylens Hernandez, Guilford, CT (US); Umut Eser, Lexington, MA (US); Michael Meyer, Guilford, CT (US); Henri Lichenstein, Guilford, CT (US); Tian Xu, Guilford, CT (US); Jonathan M. Rothberg, Guilford, CT (US)

(73) Assignee: Quantum-Si Incorporated, Branford, CT (US)

( * ) Notice: Subject to any disclaimer, the term of this patent is extended or adjusted under 35 U.S.C. 154(b) by 593 days.

(21) Appl. No.: 16/406,993

(22) Filed: May 8, 2019

(65) Prior Publication Data

US 2019/0371476 A1   Dec. 5, 2019
US 2020/0350081 A9   Nov. 5, 2020

Related U.S. Application Data

(60) Provisional application No. 62/678,094, filed on May 30, 2018.

(51) Int. Cl.
*G16H 70/40*   (2018.01)
*G16H 50/20*   (2018.01)
*G16H 50/50*   (2018.01)

(52) U.S. Cl.
CPC ............ *G16H 70/40* (2018.01); *G16H 50/20* (2018.01); *G16H 50/50* (2018.01)

(58) Field of Classification Search
CPC .... G16H 70/40; G06K 9/6215; G06K 9/6248; G06K 9/6256; G06K 9/6293
(Continued)

(56) References Cited

U.S. PATENT DOCUMENTS 5,961,924 A   10/1999   Reichert et al.
6,787,308 B2   9/2004   Balasubramanian et al.
(Continued)

FOREIGN PATENT DOCUMENTS

EP   3223183 A1   9/2017
JP   2000-310997 A   11/2000
(Continued)

OTHER PUBLICATIONS

Zhang, Ping et al. "Towards drug repositioning: a unified computational framework for integrating multiple aspects of drug similarity and disease similarity." AMIA . . . Annual Symposium proceedings. AMIA Symposium vol. 2014 1258-67. Nov. 14, 2014 (Year: 2014).*

(Continued)

*Primary Examiner* — Jonathon A. Szumny
*Assistant Examiner* — Christopher B Wehrly
(74) *Attorney, Agent, or Firm* — Wolf, Greenfield & Sacks, P.C.

(57) ABSTRACT

Methods and apparatus for predicting an association between input data in a first modality and data in a second modality using a statistical model trained to represent interactions between data having a plurality of modalities including the first modality and the second modality, the statistical model comprising a plurality of encoders and decoders, each of which is trained to process data for one of the plurality of modalities, and a joint-modality representation coupling the plurality of encoders and decoders. The method comprises selecting, based on the first modality and the second modality, an encoder/decoder pair or a pair of encoders, from among the plurality of encoders and decoders, and processing the input data with the joint-modality representation and the selected encoder/decoder pair or pair of encoders to (Continued)

predict the association between the input data and the data in the second modality.

20 Claims, 18 Drawing Sheets

(58) Field of Classification Search
USPC .......................................... 705/2, 3; 706/12
See application file for complete search history.

(56) References Cited

U.S. PATENT DOCUMENTS

| | | |
|---|---|---|
| 6,917,726 B2 | 7/2005 | Levene et al. |
| 7,175,811 B2 | 2/2007 | Bach et al. |
| 7,426,322 B2 | 9/2008 | Hyde |
| 7,738,086 B2 | 6/2010 | Shepard et al. |
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 8,053,742 B2 | 11/2011 | Lundquist et al. |
| 8,207,509 B2 | 6/2012 | Lundquist et al. |
| 8,274,040 B2 | 9/2012 | Zhong et al. |
| 8,278,728 B2 | 10/2012 | Murshid |
| 8,465,699 B2 | 6/2013 | Fehr et al. |
| 8,471,219 B2 | 6/2013 | Lundquist et al. |
| 8,471,230 B2 | 6/2013 | Zhong et al. |
| 8,502,169 B2 | 8/2013 | Rigneault et al. |
| 8,618,507 B1 | 12/2013 | Lundquist et al. |
| 9,029,802 B2 | 5/2015 | Lundquist et al. |
| 9,157,864 B2 | 10/2015 | Fehr et al. |
| 9,222,123 B2 | 12/2015 | Zhong et al. |
| 9,222,133 B2 | 12/2015 | Lundquist et al. |
| 9,223,084 B2 | 12/2015 | Grot et al. |
| 9,372,308 B1 | 6/2016 | Saxena et al. |
| 9,587,276 B2 | 3/2017 | Lundquist et al. |
| 9,606,060 B2 | 3/2017 | Chen et al. |
| 9,658,161 B2 | 5/2017 | Saxena et al. |
| 9,666,748 B2 | 5/2017 | Leobandung |
| 9,719,138 B2 | 8/2017 | Zhong et al. |
| 9,765,395 B2 | 9/2017 | Goldsmith |
| 9,946,017 B2 | 4/2018 | Saxena et al. |
| 10,018,764 B2 | 7/2018 | Grot et al. |
| 10,090,429 B2 | 10/2018 | Leobandung |
| 10,138,515 B2 | 11/2018 | Fehr et al. |
| 10,280,457 B2 | 5/2019 | Zhong et al. |
| 10,310,178 B2 | 6/2019 | Saxena et al. |
| 10,487,356 B2 | 11/2019 | Lundquist et al. |
| 10,578,788 B2 | 3/2020 | Grot et al. |
| 10,655,172 B2 | 5/2020 | Rank et al. |
| 10,724,090 B2 | 7/2020 | McCaffrey et al. |
| 10,956,787 B2 | 3/2021 | Rothberg et al. |
| 11,494,589 B2 | 11/2022 | Rothberg et al. |
| 2002/0182716 A1 | 12/2002 | Weisbuch et al. |
| 2003/0174992 A1 | 9/2003 | Levene et al. |
| 2010/0065726 A1 | 3/2010 | Zhong et al. |
| 2013/0116153 A1 | 5/2013 | Bowen et al. |
| 2015/0120760 A1* | 4/2015 | Wang .................. G06K 9/6263 707/749 |
| 2016/0170982 A1 | 6/2016 | Djuric et al. |
| 2016/0253783 A1 | 9/2016 | Higashi et al. |
| 2017/0146479 A1 | 5/2017 | Levine et al. |
| 2017/0293736 A1 | 10/2017 | Kramer et al. |
| 2019/0026655 A1 | 1/2019 | Xie et al. |
| 2019/0197366 A1* | 6/2019 | Kecskemethy .......... G06N 3/08 |
| 2019/0279075 A1 | 9/2019 | Liu et al. |
| 2019/0292590 A1 | 9/2019 | Zhong et al. |
| 2019/0347523 A1 | 11/2019 | Rothberg et al. |
| 2019/0370616 A1 | 12/2019 | Eser et al. |
| 2021/0192290 A1 | 6/2021 | Rothberg et al. |
| 2023/0039210 A1 | 2/2023 | Rothberg et al. |

FOREIGN PATENT DOCUMENTS

| | | |
|---|---|---|
| JP | 2010-152751 A | 7/2010 |
| JP | 2013-211616 A | 10/2013 |
| WO | WO 2011/153962 A1 | 12/2011 |
| WO | WO 2017/122785 A1 | 7/2017 |
| WO | WO 2018/042211 A1 | 3/2018 |

OTHER PUBLICATIONS

International Search Report and Written Opinion for International Application No. PCT/US2019/031260 dated Feb. 18, 2020.
Aliper et al., Deep learning applications for predicting pharmacological properties of drugs and drug repurposing using transcriptomic data. Molecular pharmaceutics. Jul. 5, 2016;13(7):2524-30.
Dudley et al., Computational repositioning of the anticonvulsant topiramate for inflammatory bowel disease. Science translational medicine. Aug. 17, 2011;3(94-98):119-124.
March-Vila et al., On the integration of in silico drug design methods for drug repurposing. Frontiers in pharmacology. May 23, 2017;8:298.
Masood et al., Self-supervised learning model for skin cancer diagnosis. 2015 7th International IEEE/EMBS Conference on Neural Engineering (NER). Apr. 22, 2015:1012-1015.
Napolitano et al., Drug repositioning: a machine-learning approach through data integration. Journal of cheminformatics. Dec. 1, 2013;5(1):30.
Xu et al., Comparing a knowledge-driven approach to a supervised machine learning approach in large-scale extraction of drug-side effect relationships from free-text biomedical literature. BMC bioinformatics, BioMed Central. Dec. 2015;16(5):S6.
International Search Report and Written Opinion for International Application No. PCT/US2019/031255 dated Jul. 29, 2019.
Hale, Fibre Optic Sensors using Adiabatically Tapered Single Mode Fibres. Dissertation submitted to the University of Cambridge. Feb. 1994. 209 pages.
Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.
Taitt et al., Evanescent wave fluorescence biosensors. Biosens Bioelectron. Jun. 2005;20(12):2470-87. Epub Dec. 8, 2004.

* cited by examiner

METHODS AND APPARATUS FOR MAKING BIOLOGICAL PREDICTIONS USING A TRAINED MULTI-MODAL STATISTICAL MODEL

CROSS-REFERENCE TO RELATED APPLICATIONS

This application claims priority under 35 U.S.C. § 119(e) to U.S. Provisional patent application Ser No. 62/678,094, filed May 30, 2018, and titled, "METHODS AND APPARATUS FOR MAKING BIOLOGICAL PREDICTIONS USING A TRAINED MULTI-MODAL STATISTICAL MODEL," the entire contents of which is incorporated by reference herein.

BACKGROUND

The ability to repurpose safe drugs offers great advantages to the pharmaceutical industry, including time and cost savings, and increased rate of drug approval success. The implementation of computational algorithms aiming to predict new disease indications for existing drugs or new treatments for existing diseases have recently emerged with the improvements in computer infrastructure and the advent of high throughput technologies enabling the characterization of diseases and drugs at a high resolution.

Some conventional techniques for discovering new disease indications for existing drugs or aiming to find the best drug match for a given disease or patient rely on the genomic characterization of diseases and the molecular characterization of drug's mechanism of action in order to make new predictions. These techniques can be classified as drug-based or disease-based, and although both present unique advantages and challenges, a successful computational approach usually combines aspects from both techniques.

Drug-based techniques typically focus on drug structure similarities, drug molecular activity similarity or target pathway similarity, and molecular docking. They use different information or data modalities, such as drug structures, drug targets, drug class, and gene expression perturbation upon drug treatment. Disease-based techniques typically focus on associative indication transfer, shared molecular pathology, or side effects similarities. They include information or data modalities related to disease-associated mutations and pathways, and disease-associated changes in gene expression, or proteins, or metabolites, or microbiome. Examples of approaches combining both drug-based and disease-based rationales include: transcription signature complementarity and drug target-disease pathway similarity.

SUMMARY

According to one aspect of the technology described herein, some embodiments are directed to a method for training a statistical model configured to represent inter-modality associations between data in a heterogeneous network. The method comprises accessing training data including training data for a first modality and training data for a second modality different from the first modality, training the statistical model, the statistical model comprising first and second encoders, first and second decoders, and a joint-modality representation coupling the first and second encoders to the first and second decoders. The training comprises estimating values for parameters of the first and second encoders and the first and second decoders using a self-supervised learning technique, at least some of the training data, and information describing at least one link between data pairs in the training data, and storing information specifying the statistical model at least in part by storing the estimated values for parameters of the first and second encoders and the first and second decoders of the statistical model.

According to another aspect of the technology described herein, some embodiments are directed to a method for predicting an association between input data in a first modality and data in a second modality using a statistical model trained to represent links between data having a plurality of modalities including the first modality and the second modality, the statistical model comprising a plurality of encoders and decoders, each of which is trained to process data for one of the plurality of modalities, and a joint-modality representation coupling the plurality of encoders and decoders. The method comprises selecting, based on the first modality and the second modality, an encoder/decoder pair or a pair of encoders, from among the plurality of encoders and decoders, and processing the input data with the joint-modality representation and the selected encoder/decoder pair or pair of encoders to predict the association between the input data and the data in the second modality.

According to another aspect of the technology described herein, some embodiments are directed to a method for predicting associations between data in a first modality and data in a second modality using a statistical model trained to represent interactions between data having a plurality of modalities including the first modality and the second modality, the statistical model comprising a plurality of encoders and decoders, each of which is trained to process data for one of the plurality of modalities, and a joint-modality representation coupling the plurality of encoders and decoders. The method comprises mapping the data in the first modality and the data in the second modality into a common representation space within the statistical model, accessing a statistical classifier trained using labeled data, wherein the labeled data describes associations between data in the first and second modalities, and predicting associations between the data in the first modality and the data in the second modality mapped into the common representation space using the trained statistical classifier.

According to another aspect of the technology described herein, some embodiments are directed to a computer system, comprising at least one computer processor and at least one storage device encoded with a plurality of instructions that, when executed by the at least one computer processor perform a method of training a statistical model to represent inter-modality associations for data, wherein the data includes data for a first modality and data for a second modality different from the first modality. The method comprises accessing training data including training data for the first modality and training data for the second modality, training the statistical model, the statistical model comprising first and second encoders, first and second decoders, and a joint-modality representation coupling the first and second encoders to the first and second decoders. The training comprises estimating values for parameters of the first and second encoders and the first and second decoders using a self-supervised learning technique, at least some of the training data, and information describing at least one link between data pairs in the training data, and storing information specifying the statistical model at least in part by storing the estimated values for parameters of the first and second encoders and the first and second decoders of the statistical model.

According to another aspect of the technology described herein, some embodiments are directed to a computer system comprising at least one computer processor and at least one storage device encoded with a plurality of instructions that, when executed by the at least one computer processor perform a method of predicting an association between input data in a first modality and data in a second modality using a statistical model trained to represent interactions between data having a plurality of modalities including the first modality and the second modality, the statistical model comprising a plurality of encoders and decoders, each of which is trained to process data for one of the plurality of modalities, and a joint-modality representation coupling the plurality of encoders and decoders. The method comprises selecting, based on the first modality and the second modality, an encoder/decoder pair or a pair of encoders, from among the plurality of encoders and decoders, and processing the input data with the joint-modality representation and the selected encoder/decoder pair or pair of encoders to predict the association between the input data and the data in the second modality.

According to another aspect of the technology described herein, some embodiments are directed to a computer system comprising at least one computer processor and at least one storage device encoded with a plurality of instructions that, when executed by the at least one computer processor, perform a method of predicting associations between data in a first modality and data in a second modality using a statistical model trained to represent links between data having a plurality of modalities including the first modality and the second modality different from the first modality, the statistical model comprising a plurality of encoders and decoders, each of which is trained to process data for one of the plurality of modalities, and a joint-modality representation coupling the plurality of encoders and decoders. The method comprises mapping the data in the first modality and the data in the second modality into a common representation space within the statistical model, accessing a statistical classifier trained using labeled data, wherein the labeled data describes associations between data in the first and second modalities, and predicting associations between the data in the first modality and the data in the second modality mapped into the common representation space using the trained statistical classifier.

According to another aspect of the technology described herein, some embodiments are directed to a method for training a statistical model to represent associations between drug data, gene data, and disease data. The method comprises accessing training data including gene training data, drug training data and disease training data, and training the statistical model, the statistical model comprising a plurality of encoders including a gene encoder, a drug encoder and a disease encoder, a plurality of decoders including a gene decoder, a drug decoder and a disease decoder, and a joint representation coupling the plurality of encoders to the plurality of decoders, wherein the joint representation describes interactions between the training data. The training comprises estimating values for parameters of the gene encoder and the gene decoder using a self-supervised learning technique, the gene training data, and information describing interactions between data pairs in the gene training data, estimating values for parameters of the gene encoder, the gene decoder, the drug encoder, and the drug decoder using a self-supervised learning technique, the gene training data and the drug training data, and information describing interactions between data elements in the gene training data and data elements in the drug training data, estimating values for parameters of the gene encoder, the gene decoder, the disease encoder, and the disease decoder using a self-supervised learning technique, the gene training data and the disease training data, and information describing interactions between data elements in the gene training data and data elements in the disease training data, and storing information specifying the statistical model at least in part by storing the estimated values for parameters of the gene encoder, the gene decoder, the drug encoder, the drug decoder, the disease encoder, and the disease decoder of the statistical model.

According to another aspect of the technology described herein, some embodiments are directed to a computer system, comprising at least one computer processor and at least one storage device encoded with a plurality of instructions that, when executed by the at least one computer processor perform a method of training a statistical model to represent associations between drug data, gene data, and disease data. The method comprises accessing training data including gene training data, drug training data and disease training data, and training the statistical model, the statistical model comprising a plurality of encoders including a gene encoder, a drug encoder and a disease encoder, a plurality of decoders including a gene decoder, a drug decoder, and a disease decoder, and a joint representation coupling the plurality of encoders to the plurality of decoders, wherein the joint representation describes interactions between the training data. The training comprises estimating values for parameters of the gene encoder and the gene decoder using a self-supervised learning technique, the gene training data, and information describing interactions between data pairs in the gene training data, estimating values for parameters of the gene encoder, the gene decoder, the drug encoder, and the drug decoder using a self-supervised learning technique, the gene training data and the drug training data, and information describing interactions between data elements in the gene training data and data elements in the drug training data, and estimating values for parameters of the gene encoder, the gene decoder, the disease encoder, and the disease decoder using a self-supervised learning technique, the gene training data and the disease training data, and information describing interactions between data elements in the gene training data and data elements in the disease training data, and storing information specifying the statistical model at least in part by storing the estimated values for parameters of the gene encoder, the gene decoder, the drug encoder, the drug decoder, the disease encoder, and the disease decoder of the statistical model.

According to another aspect of the technology described herein, some embodiments are directed to a method for predicting a new disease indication for a given drug. The method comprises projecting a representation of the given drug and representations of a plurality of diseases into a common representation space of a trained statistical model and predicting the new disease indication for the given drug based on a comparison of the projected representation of the given drug and at least one of the representations of the plurality of diseases in the common representation space.

According to another aspect of the technology described herein, some embodiments are directed to a computer system, comprising at least one computer processor; and at least one storage device encoded with a plurality of instructions that, when executed by the at least one computer processor, performs a method of predicting a new disease indication for a given drug. The method comprises projecting a representation of the given drug and representations of a plurality of diseases into a common representation space of a trained statistical model, and predicting the new disease indication for the given drug based on a comparison of the projected representation of the given drug and at least one of the representations of the plurality of diseases in the common representation space.

According to another aspect of the technology described herein, some embodiments are directed to a method of identifying disease indications for a given drug. The method comprises providing as input to a statistical model, representations of a plurality of drugs and a plurality of diseases, and processing the representations of the plurality of drugs and the plurality of diseases using a trained supervised classifier to identify a likelihood that drugs in the plurality of drugs will be effective in treating diseases in the plurality of diseases, the supervised classifier trained with information on Federal Drug Administration (FDA) approved drug-disease pairs.

According to another aspect of the technology described herein, some embodiments are directed to a computer system, comprising at least one computer processor and at least one storage device encoded with a plurality of instructions that, when executed by the at least one computer processor, performs a method of identifying disease indications for a given drug. The method comprises providing as input to a statistical model, representations of a plurality of drugs and a plurality of diseases, and processing the representations of the plurality of drugs and the plurality of diseases using a trained supervised classifier to identify a likelihood that drugs in the plurality of drugs will be effective in treating diseases in the plurality of diseases, the supervised classifier trained with information on Federal Drug Administration (FDA) approved drug-disease pairs.

It should be appreciated that all combinations of the foregoing concepts and additional concepts discussed in greater detail below (provided such concepts are not mutually inconsistent) are contemplated as being part of the inventive subject matter disclosed herein.

BRIEF DESCRIPTION OF THE DRAWINGS

Various non-limiting embodiments of the technology will be described with reference to the following figures. It should be appreciated that the figures are not necessarily drawn to scale.

DETAILED DESCRIPTION

Figure 1:
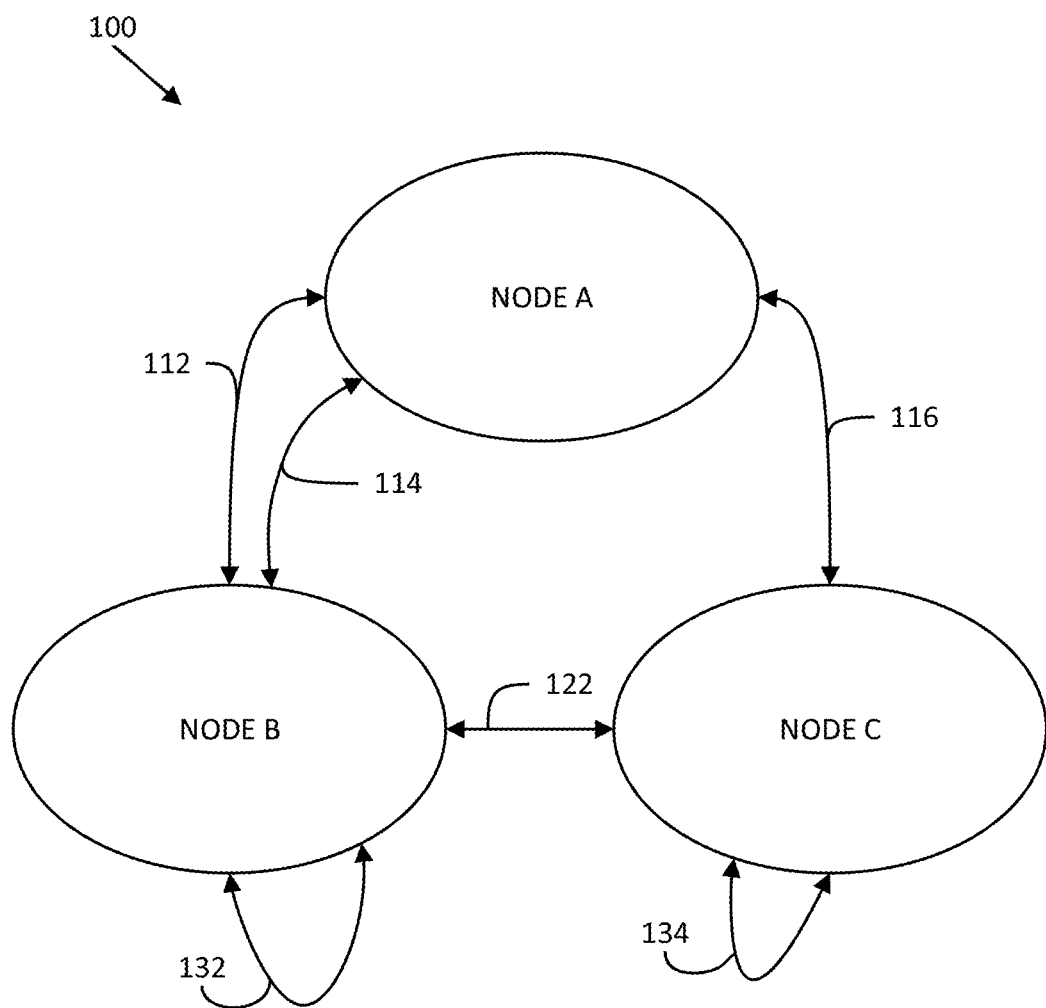
FIG. 1 is a diagram of a heterogeneous network in accordance with some embodiments.

Conventional computational approaches to predict associations between biological data (e.g., drug-disease matches) using statistical or machine learning techniques typically employ supervised learning techniques. The data set available for training such techniques is often limited to a relatively small amount of labeled data (e.g., FDA approved drugs). Such approaches are also typically focused on one or two modalities (e.g., drugs and diseases), and do not consider information from other modalities during training or in making predictions. To this end, some embodiments are directed to a scalable technique for integrating biological information from multiple modalities to incorporate biological (e.g., drug and/or disease) information from a wide range of sources. In particular, some embodiments are directed to representing a heterogeneous network of multimodal biological information using one or more statistical models configured learn connections between the data in the model using a self-supervised learning technique. A schematic example of a heterogeneous network that may be represented using a statistical model in accordance with some embodiments is shown in FIG. 1.

As shown, heterogeneous network 100 includes a plurality of nodes and connections between the nodes. Each of the nodes in the network 100 is associated with data having a different modality. For example, node A may represent data associated with diseases, node B may represent data associated with genes, and node C may represent data associated with drugs. The links associated with the nodes in network 100 include intra-modality links (e.g., links 132, 134) that describe interactions between data within a single modality. For example, link 132 describes an interaction between data associated with node B (e.g., genes interacting with other genes) and link 134 describes an interaction between data associated with node C (e.g., drugs having structural similarity to other drugs). Each node in the heterogeneous network may include any suitable number of intra-modality links (including no intra-modality links), and the number of links associated with any one node in the network may be dependent on the modality of the data associated with the node. For example, as discussed in more detail below, a node associated with the "gene" modality may have more intra-modality links than a node associated with the "drug class" modality.

Each node in network 100 also includes at least one inter-modality link (e.g., links 112, 114, 116 and 122) that describe an interaction between data from different modalities. The inter-modality link(s) connect the node to other node(s) in the network. Whereas some nodes only include a single inter-modality link, other nodes include multiple inter-modality links to one or more other nodes indicating more complex associations between the data in network 100. By virtue of the inter-modality links in network 100, associations between data from disparate data sources in the network may be learned in some embodiments to enable predictions between nodes that are directly or indirectly connected via other nodes in the network. For example, the association between data in node A and node C may be learned via the direct link 116 between these two nodes as well as indirect paths between node A and node C via node B (e.g., via links 112, 114 and 122). The mesh of learned connections between data represented by the nodes in network 100 adds to the richness of the data representation encoded using a trained statistical model in accordance with some embodiments. For example, the trained statistical model may be used to predict missing links within the heterogeneous drug-disease network.

Figure 2:
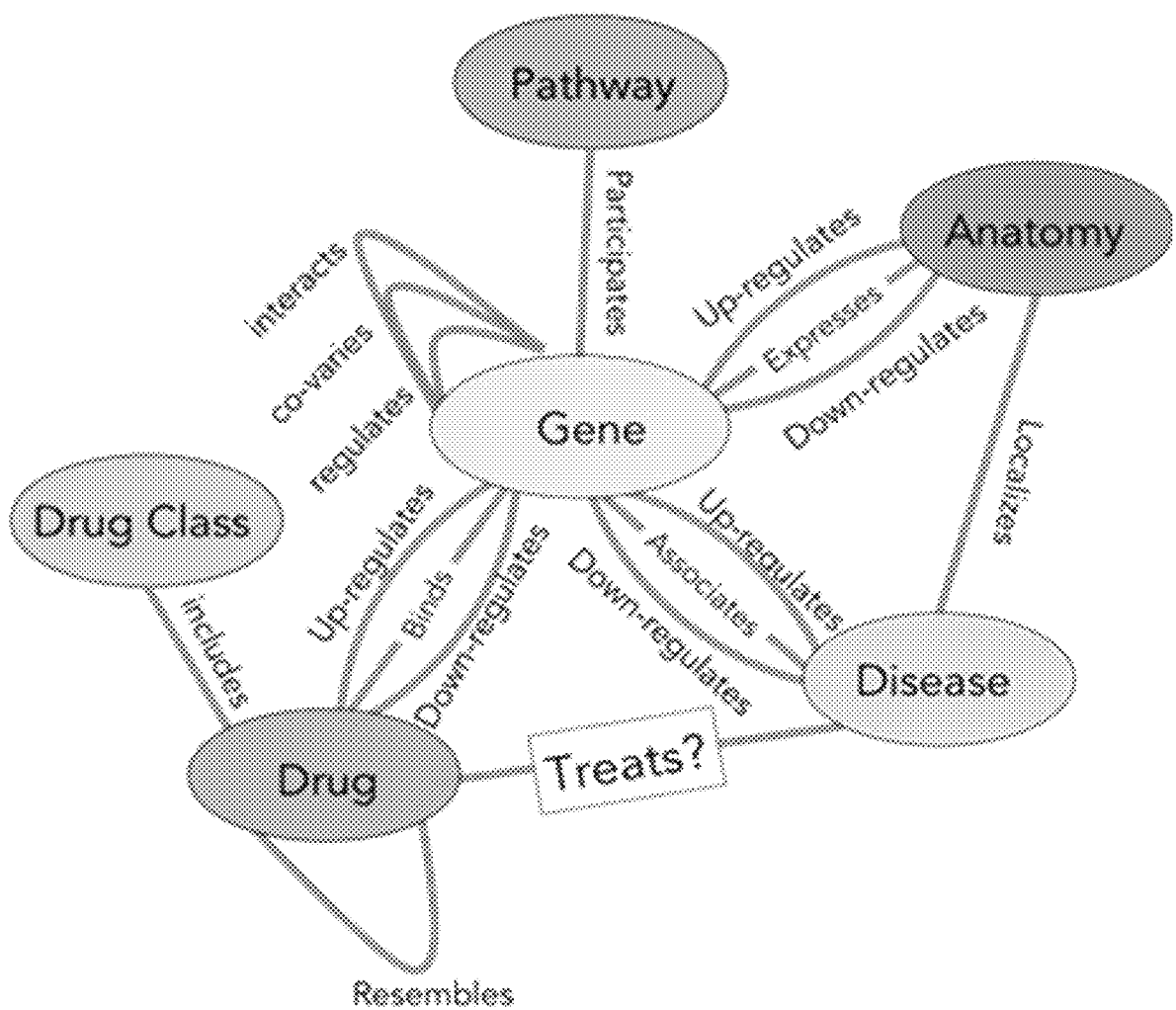
FIG. 2 is a diagram of a heterogeneous network of biological data that may be represented using a multi-modal statistical model in accordance with some embodiments.

FIG. 2 shows an example of a drug-disease heterogeneous network that may be represented using a statistical model in accordance with some embodiments. As shown, the network includes a plurality of nodes, each of which is associated with biological data for a different modality. The network includes intra-modality and inter-modality links associated with and connecting the nodes in the network. The links describe how pairs of data within a modality or from different modalities are related to each other. By including multiple nodes in a heterogeneous network, relationships between drugs and diseases can be established through multiple modalities, such as genes affected by a disease or associated with disease, genes regulated by drugs or targeted by drugs, and genes expressed in disease-affected tissues. Additionally, drugs can be characterized by their molecular structure, their respective protein targets, drug class, and side effects, whereas diseases can also be characterized by disease ontology.

In the particular drug-disease network shown in FIG. 2, the node associated with genes represents core functional links between drugs and diseases by being connected directly with four other nodes in the network. Genes may be characterized by functional interactions, such as protein-protein interactions, transcriptional regulation or co-expression networks, and their respective biological pathways or gene ontology associations. In some embodiments, the network includes one or more of drug- and disease-metabolomics, proteomics, and microbiome information.

As additional biological data becomes available, the drug-disease heterogeneous network shown in FIG. 2 may be expanded to include additional nodes and/or additional links between the nodes. In such a way, the representation of the drug-disease heterogeneous network is easily extensible and scalable, unlike some conventional computational models trained to make predictions based on data from only one or two modalities. New nodes or types of data represented within existing nodes of the heterogeneous network may be added in any suitable way. For example, in some embodiments, nodes within the drug-disease heterogeneous network may include data associated with different organisms (e.g., data from human and mouse datasets). Drug-phenotype associations from model organisms, from *Saccharomyces cerevisiae* (yeast), *Caenorhabditis elegans* (worm), *Danio rerio* (zebrafish), *Arabidopsis thaliana* (thale or mouse-ear cress) and *Drosophila melanogaster* (fruit fly) may also be included. In another example, inter-organism connections may be represented in the model using orthologous gene associations.

The data associated with the nodes in the heterogeneous network may be identified from any data source that provides reliable information about the interactions between data within a particular modality (e.g., gene-gene interactions) or between data from different modalities (e.g., drug treatments for diseases). In some embodiments, information about the interactions of data with the heterogeneous network are determined based on information in publically-accessible databases and/or proprietary databases of biological information or based on the results of clinical trials or other medical research. For example, data associated with drugs may include information related to small molecules and/or biologics and data associated with diseases may include information related to disease categories including, but not limited to, neoplasms (e.g., leukemia, lymphoma, lung cancer, melanoma, thyroid cancer, hepatic cancer, prostate cancer, kidney or renal cancer, pancreatic cancer, intestine cancer, glioblastoma, astrocytomas, breast cancer, among others) and non-cancer diseases (e.g., neurological, cardiovascular, dermatological, musculoskeletal, urologics, respiratory, nutritional and metabolic diseases, etc.).

A drug-disease heterogeneous network used in accordance with some embodiments may also include information related to gene-gene interactions derived from synthetic lethal screens and gene-disease interactions derived from Crispr- or shRNA or siRNA screening. Additionally, information about direct interactions between drugs and diseases may be determined based, at least in part, on information about FDA approved drugs—disease indications and in vitro cancer cell line viability experiments.

Table 1 provides a listing of example datasets and databases that may be used to identify data and interactions for a heterogeneous network in accordance with some embodiments. As described in more detail below, information about interactions between data extracted from these data sources (and others) may be used to train a statistical model such that the trained statistical model is configured to represent inter-modality associations in the heterogeneous network. The trained statistical model may then be used to make new inter-modality predictions.

TABLE 1

Example databases used for building a drug-disease heterogeneous network.

| Dataset | Database |
| --- | --- |
| Drug expression profiles | CMAP-LINCS-L1000 |
| Drug targets, structure, and class | ChEMBL, ChemSpider, PubChem, DrugsDB, DrugCentral |
| Disease expression profile | TCGA |
| Disease-gene association (mutation) | COSMIC db, OMIM db, intogen db |
| Disease-anatomy association | Medline V1.0 (Himmelstein DS. 2016) |
| Gene-Pathway associations | KEGG, Reactome, WikiPathway, Gene Ontology |

TABLE 1-continued

Example databases used for building
a drug-disease heterogeneous network.

| Dataset | Database |
| --- | --- |
| Gene-Anatomy association/regulation | GTEx Portal, TISSUES, Bgee |
| Protein-Protein interactions | StringDB, Human Interaction Database, and the Human Protein Reference Database |
| Gene regulatory interactions | CMAP-LINCS-L1000 |

As discussed above in connection with FIG. 2, each node in the heterogeneous network includes at least one link to one or more other nodes in the network. Some embodiments are directed to encoding these links between data in the network by training a statistical model using information about pairs of data extracted from data sources including, but not limited to, the data sources listed in Table 1.

Each of the nodes and its associated links (both intra-modality and inter-modality) in the network of FIG. 2 may be considered separately for training a statistical model in accordance with some embodiments. Each of the links between data for nodes in the network may be represented using categorical features. The categorical features enable the data for each modality to be mapped to a vector having continuous values using a data embedding technique described in more detail below. The vectors are then provided as input to the statistical model during a training phase and may be used for prediction following training.

In some instances, interactions between data in the heterogeneous network may be represented using only categorical features. For example, in the interaction "drug-treats-disease," a particular drug may either be approved to treat a particular disease or not approved. In other words, the "treats" interaction is binary. In other instances, interactions between data in the heterogeneous network may additionally be represented using numerical features that indicate a strength of the interaction between the linked data. For example, in the interaction "drug-regulates-gene," categorical features may be used to represent whether a particular drug regulates a particular gene based, for example, on drug expression profiles, and numerical features may be used to represent the extent or strength of the regulation as determined, for example, based on differential gene expression comparisons.

Example interactions associated with the heterogeneous network shown in FIG. 2 are described in more detail below including an indication of which data from the example databases in Table 1 was used to determine the interaction data and whether the interaction was represented in the heterogeneous network using only categorical features or numerical features in addition to categorical features. The interactions in the network of FIG. 2 are described below by computing interaction metrics in exemplary ways. However, it should be appreciated that any or all of the interaction metrics may be extracted and/or computed from data sources in any suitable way, and embodiments are not limited in this respect.

Drug-Centered Interactions

As shown in FIG. 2, the "drug" node includes six different drug-centered interactions including one intra-modality interaction (drug-resembles-drug) and five inter-modality interactions that connect the drug node to other nodes in the network. The intra-modality "drug-resemble-drug" interaction, which is defined by both categorical and numerical features, describes pairwise structural similarities of drugs in the network. For example, the "resemble" metric may be computed by calculating the pairwise drug structure similarity from drug-corresponding fingerprints, based on the Tanimoto coefficient and using the python library RDKit (http://www.rdkit.org). In one implementation, drug structures were downloaded from three different databases (ChEMBL, ChemSpider, PubChem) in the form of "smiles", followed by smile standardization using the python library MolVS (https://molvs.readthedocs.io/). Next, the molecular fingerprints for each drug were computed and the Tanimoto coefficient from all possible pairwise drug fingerprints comparisons was calculated to determine which drugs resembled other drugs.

The "drug-regulates-gene" interaction is defined by both categorical and numerical features. This interaction may be determined based on drug expression profiles extracted, for example, from the CMAP-LINCS-L1000 database. In one implementation, the data was downloaded from the Gene Expression Omnibus database (Accession ID=GSE92742), and contained a total of 19811 drugs that were screened in triplicate at two different time points (6 hours and 24 hours) in a variable set of 3-77 well annotated cell lines. The gene expression data used in this implementation included level 5 processed data, containing for each cell line, time point and drug treatment, the normalized differential gene expression values with respect to the control conditions. The data may be represented by a vector (e.g., of dimension 1×12328) of genes and their corresponding Z-scores for each combination of cell line, time point and drug treatment.

Additionally, drug-induced gene expression data was generated for multiple drugs from a proprietary database. These profiles were generated in seven different cancer cell lines, at two different time points (6 hours and 24 hours) and at two different concentrations for each drug. The differential gene expression was normalized with respect to the control condition, and processed in the form of a Z-score. The data generated for drugs from the proprietary database had the same structure as the CMAP-LINCS-L1000's data.

As noted above, the "drug-treats-disease" interaction is categorical. This interaction may be based on a list of approved (e.g., FDA approved) drugs and their corresponding disease indications. In one implementation, data for this interaction was downloaded from the PharmacotherapyDB database and contained 755 disease-drug pairs.

The "drug-includes-drug class" interaction is categorical. This interaction describes the correspondence between each drug and its pharmacologic class. In one implementation, data for this interaction was downloaded from the DrugBank (https://www.drugbank.ca/) and DrugCentral (http://drugcentral.org) databases.

The "drug-binds-gene" interaction is categorical. This interaction describes the relationship between drugs and their protein targets, encoded by genes. In one implementation, data for this interaction were obtained from the DrugBank (https://www.drugbank.ca/), DrugCentral (http://drugcentral.org), and BindingDB (https://www.bindingdb.org) databases.

Disease-Centered Interactions

As shown in FIG. 2, the "disease" node includes five different disease-centered inter-modality interactions (one of which is the "drug-treats-disease" interaction described above) that connect the disease node to other nodes in the network. The disease node is not associated with any intra-modality interactions. The "disease-regulates-gene" interaction is represented using both categorical and numerical features. In one implementation, data for this interaction was obtained from the TCGA database (https://tcga-data.nci.nih.gov/) and from a proprietary database. This interaction relates to genes that are up- and down-regulated in diseased tissue when compared to matching normal control tissue or healthy individuals. The TCGA database contains cancer gene expression profiles and their matching normal control tissue profile for each patient. In one implementation, both profiles for each patient were downloaded, the corresponding fold change between tumor and control was calculated, and the gene expression values were normalized to Z scores. A proprietary database containing approximately 1500 gene expression profiles from 575 different diseases (cancer and non-cancer disease indications) was also used to generate data for the "disease-regulates-gene" interaction. Data from the Gene Expression Omnibus Database (https://www.ncbi.nlm.nih.gov/geo/) was downloaded and processed using the R libraries GEOquery and Limma. Each disease expression profile was normalized with Limma, followed by gene fold change calculation between disease and normal cases. Proprietary disease gene expression profiles were also normalized to Z-scores.

The "disease-associates-gene" interaction is categorical. This interaction relates to gene-specific mutations associated to a particular disease. In one implementation, the associations of gene mutations corresponding to Mendelian diseases were downloaded from the OMIM database (https://www.omim.org/). The associations of gene mutations corresponding to specific cancers were downloaded from the COSMICdb (https://cancer.sanger.ac.uk/cosmic) and Intogen databases (https://www.intogen.org/).

The "disease-localizes-anatomy" interaction is categorical. This interaction relates to the association between diseases and corresponding human tissues affected by disease. In one implementation, these relationships were downloaded from the Medline disease-tissue association (Himmelstein DS. 2016) database. Anatomical terms were mapped to anatomical structures ontology terms (http://uberon.github.io, Mungall et al, 2012).

Gene-Centered Interactions

As shown in FIG. 2, the "gene" node includes thirteen different gene-centered interactions including three intra-modality interactions and ten inter-modality interactions (six of which are described above in connection with the drug- and disease-centered interactions) that connect the gene node to other nodes in the network. The intra-modality "gene-interacts with-gene" interaction is categorical and relates to physical protein-protein interactions downloaded, for example, from StringDB (https://string-db.org/), the Human Interaction Database (http://interactome.dfci.harvard.edu/), and the Human Protein Reference Database (http://www.hprd.org).

The intra-modality "gene-regulates-gene" interaction is represented using both categorical and numerical features. This interaction relates to normalized gene expression levels across different cancer cell lines with respect to knockdown or overexpression of specific genes. In one implementation, this data was downloaded from CMAP-LINCS-L1000, and the gene expression values were normalized in Z-scores.

The intra-modality "gene-covaries with-gene" interaction is represented using both categorical and numerical features. This interaction relates to the rate of evolutionary covariation between genes. In one implementation, the data for this interaction was downloaded from Priedigkeit et al, 2015. Insight for including this interaction in the network is derived from the observation that genes that tend to co-evolve together are generally involved in similar biological pathways and therefore may participate in similar diseases.

The "gene-expresses in-anatomy" interaction is categorical and includes expression levels of genes in specific human tissue types. In one implementation, data for this interaction were downloaded from the TISSUES database (https://tissuesjensenlab.org/) and the GTEx Portal (https://www.gtexportal.org/). The TISSUES database combines data from gene expression, immunohistochemistry, proteomics and text mining experiments, whereas the GTEx Portal contains RNA-sequence data from multiple human tissues.

The "gene regulated by anatomy" interaction is categorical and includes gene regulation information (e.g., up- and down-regulation) in specific tissue types. In one implementation, data for this interaction were extracted from the Bgee database, for adult humans (https://bgee.org/) and the GTEx Portal.

The "gene-participates in-pathway" interaction is categorical and relates to the association between genes and their corresponding cellular pathways. In one implementation, the molecular function, cellular localization and biological process were downloaded from the Gene Ontology Consortium (http://www.geneontology.org). The associations corresponding to metabolic, and signaling pathways were obtained from KEGG (www.genome.jp/kegg/), Reactome (https://reactome.org), and WikiPathways (https://wikipathways.org/).

Although six nodes are shown in the illustrative heterogeneous network of FIG. 2, it should be appreciated that a heterogeneous network including additional (or fewer) nodes may alternatively be represented using one or more statistical models in accordance with some embodiments. For example, some embodiments are directed to representing a heterogeneous network including only the three nodes "drug," "gene," and "disease" and their corresponding intra- and inter-modality links by a statistical model. In other embodiments, a heterogeneous network having at least one node representing patient data (e.g., from an electronic health record) is represented using a statistical model.

Some embodiments are directed to a multi-modal representation that integrates all domains and modalities from a heterogeneous network of biological data, an example of which is described above in connection with FIG. 2. Unlike some conventional approaches that rely on supervised learning and a limited training data set, some embodiments employ self-supervised learning techniques that do not require large paired datasets for training. As discussed in more detail below, the statistical model is trained in some embodiments to take advantage of shared connections between drugs and diseases, such as genes, in order to find novel drug-disease associations.

Figure 3:
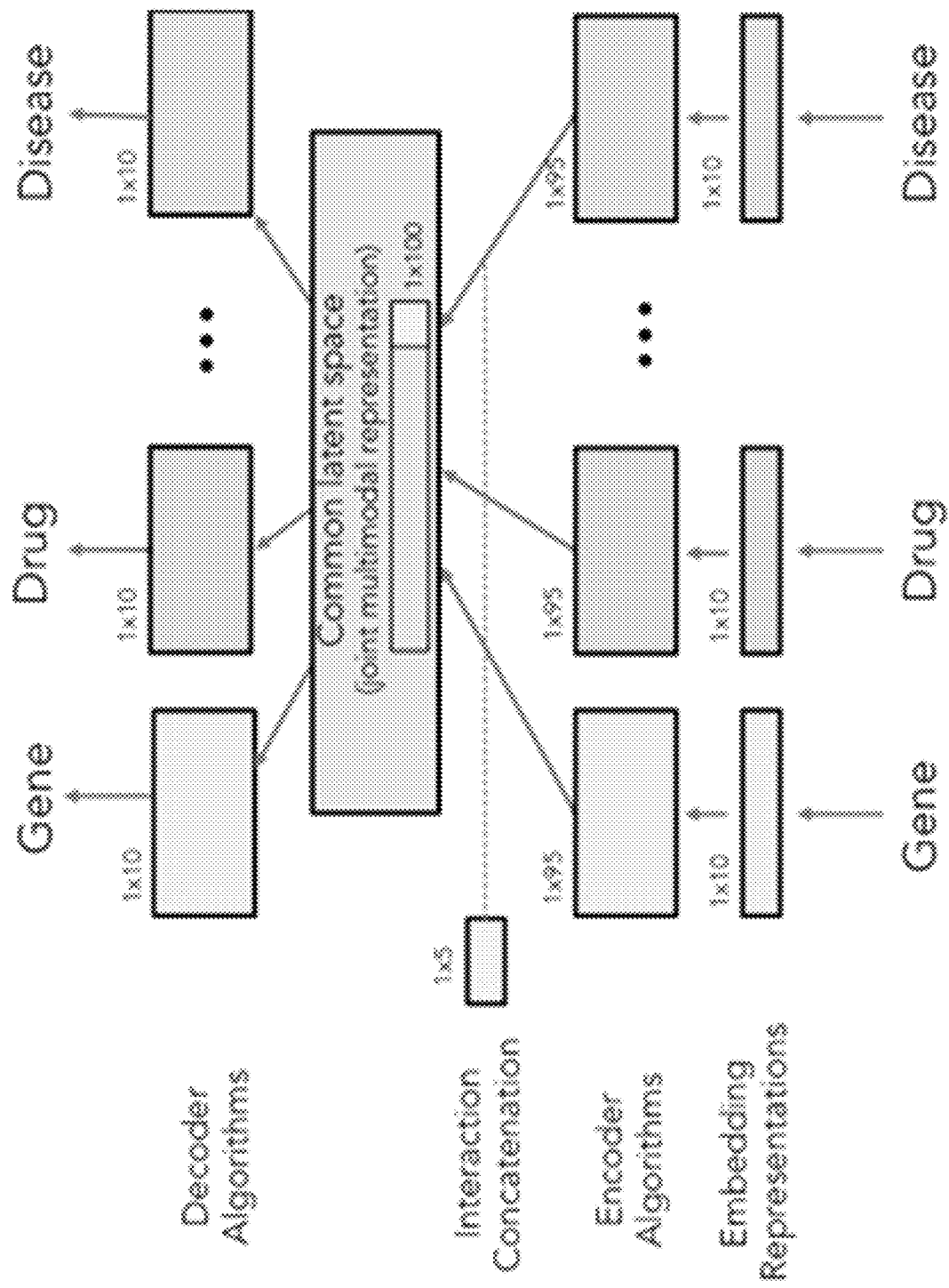
FIG. 3 is a diagram of a model architecture for representing a heterogeneous network of biological data in accordance with some embodiments.

FIG. 3 schematically illustrates a high-level architecture of a statistical model that may be trained using self-supervised learning techniques in accordance with some embodiments. Each of the nodes corresponding to a different modality in a heterogeneous network is represented as a separate path from input to output through the architecture. Only "gene," "drug," and "disease" modalities are represented in the architecture of FIG. 3. However, it should be appreciated that other modalities including, but not limited to, the other nodes in the heterogeneous network of FIG. 2, may also be included in the model architecture shown in FIG. 3.

As shown, the architecture of FIG. 3 includes a plurality of encoder/decoder pairs, each of which is configured to employ a self-supervised learning technique to train values for parameters of the unimodal encoder/decoder pair. The number of encoder/decoder pairs included in the architecture depends on the number of modalities or nodes included in the heterogeneous network. The encoder/decoder pairs are joined using a common latent space (also referred to herein as a joint-modality representation or joint multimodal representation) to form a multi-modal statistical model that is able to learn joint representations of each network node and its corresponding network links, as described in more detail below.

As shown in FIG. 3, for each encoder/decoder pair, the architecture includes a plurality of embedding representations, which are vectors of continuous values that are a transformation of the categorical input data. The encoders and decoders in each encoder/decoder pair are coupled via a joint-modality representation, which includes joint representation vectors of connected network nodes in the heterogeneous network. The number of vectors in the joint-modality representation is equal to the number of interactions in the network such that the joint-modality representation may be represented as an N×D matrix, where N is the number of interactions in the network and D is a length of each joint representation vector. In some embodiments, $N > 1 \times 10^6$. Information about interactions between data in the network is encoded in the joint-modality representation. The interactions may be encoded in any suitable way. In some embodiments, an embedding interaction vector representing a particular interaction between data in an input pair may be created and concatenated to a corresponding joint representation vector in the common latent space. In other embodiments, rather than concatenating an embedding interaction vector to the joint representation vector, the embedding interaction vector may be concatenated to the output from two encoders from which the joint representation vector is created. In yet other embodiments, the interaction information may be intrinsically encoded by virtue of a joint representation vector being formed from the output of two encoders to which particular input data having a particular interaction was provided.

As discussed in more detail below, for intra-modality (e.g., gene-gene) interactions, each of the encoder/decoder pairs is trained using a self-supervised learning technique, pairs of input data within the modality associated with a node in the heterogeneous network, and interaction information describing an interaction between the pairs of data. For inter-modality (e.g., gene-drug) interactions, two encoder/decoder pairs are trained using a self-supervised learning technique, pairs of input data across the two modalities, and interaction information describing an interaction between the input data from the different modalities. When the interaction includes both categorical and numerical features, the numerical features may be taken into account by, for example, multiplying the embedding interaction vector and/or all or a portion of the joint representation vector by a value corresponding to the strength or degree of the interaction as represented in the numerical features.

Figure 4:
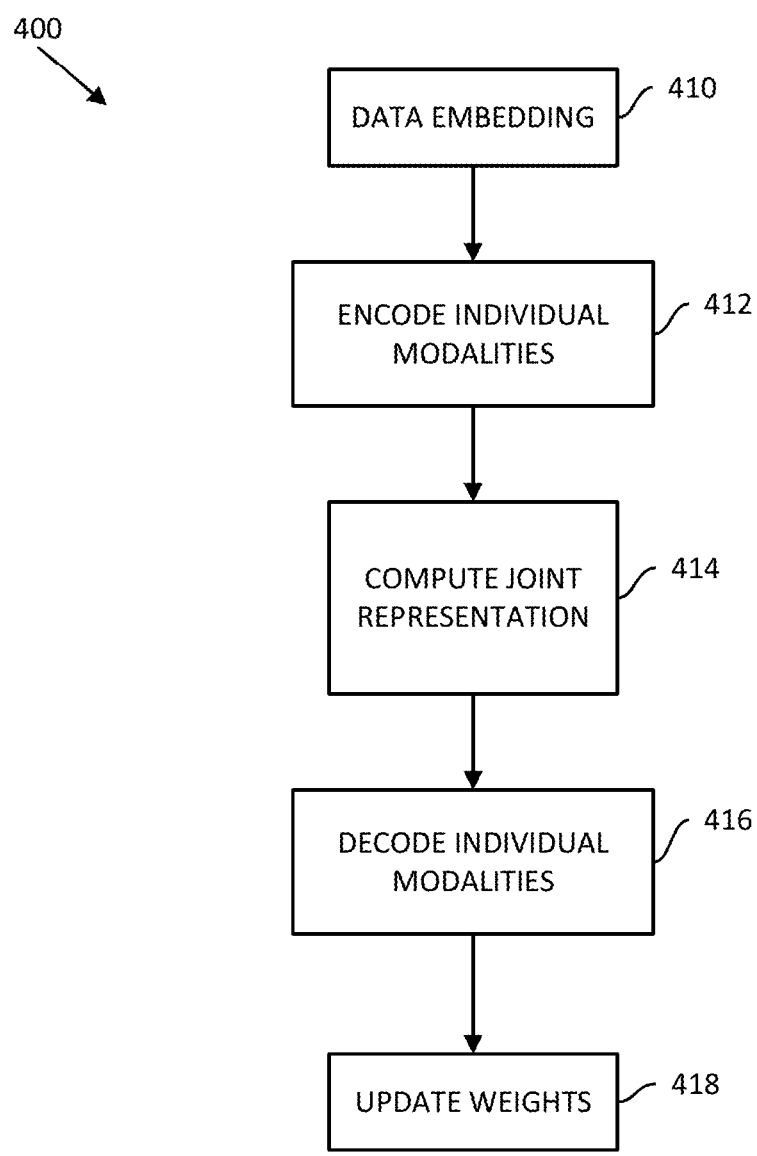
FIG. 4 is a flowchart of a process for training a statistical model to represent a heterogeneous network of biological data in accordance with some embodiments.

FIG. 4 illustrates a process 400 for training a multi-modal statistical model having an architecture shown in FIG. 3, in accordance with some embodiments. In act 410, training data (e.g., extracted from one or more public or proprietary data sources such as those in Table 1) is converted into embedding vectors that are to be provided as input to encoders. During data embedding, related categorical variables are represented by dense vectors of real numbers that capture the relationship between them. The embedding vectors represent each variable in a continuous numerical space. Creation of embedding vectors are described in more detail in connection with FIG. 5.

Process 400 then proceeds to act 412, where the embedding vectors are provided as input to a modality-specific encoder to provide an encoded output vector in the joint-modality representation space. Process 400 then proceeds to act 414, where a joint representation vector is computed based, at least in part, on the encoded output vectors output from two encoders. The joint representation vector may additionally be computed based, at least part, on information describing an interaction between the input data, such as an embedding interaction vector, as described above. Process 440 then proceeds to act 416, where the joint representation vector is provided as input to a modality-specific decoder to generate a decoded output vector. Process 400 then proceeds to act 418, where the weights in the encoders and decoders are updated based, at least in part, on a comparison of the decoded output vector and the embedded vector provided as input to the modality-specific encoder. For example, a self-supervised learning technique is used to update values of parameters (e.g., weights) in the encoder and decoder during training. Each of the acts described in process 400 is described in more detail below.

Figure 5:
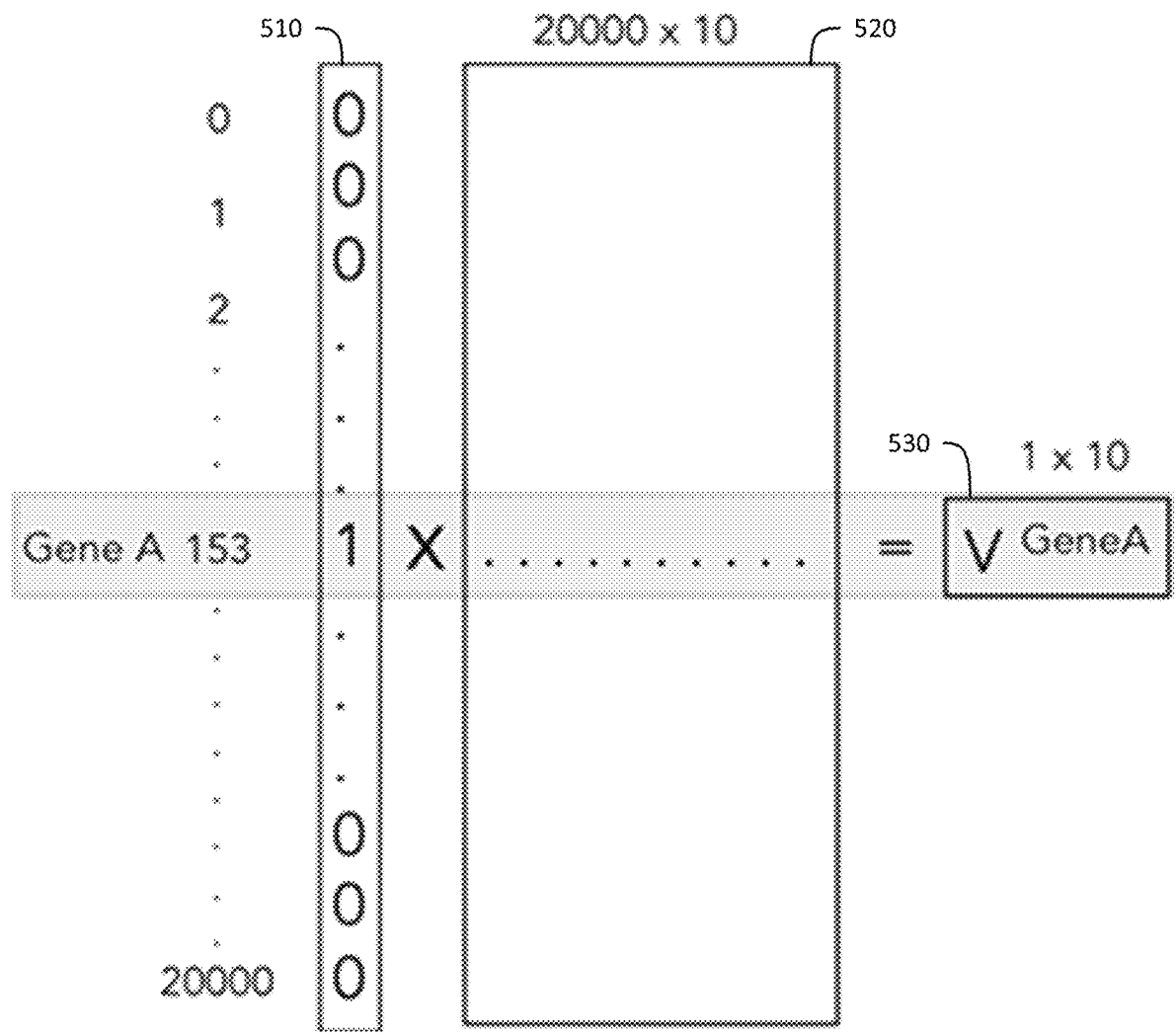
FIG. 5 is a diagram of a process for performing data embedding in accordance with some embodiments.

FIG. 5 shows a process for generating embedding vectors for input data associated with a node in a heterogeneous network using categorical features in accordance with some embodiments. An input dimension V is defined for each modality that corresponds to the size of the vocabulary of the data in the modality. In the example shown in FIG. 5, the modality is "gene" and the size of the vocabulary V is 20,000 indicating that there are 20,000 genes in the input dataset. Each element of the modality is "represented" by a one-hot vector 510 of length V, with the ith element having a value of 1, with all other elements in the vector being set to 0. For example, to encode the input data element "Gene A," the value of position 153 in the one-hot vector 510 is set to 1, while all of the other values in the vector are set to 0. A separate one-hot vector is created for each of the elements (e.g., each of the 20,000 genes in the example of FIG. 5) in the input data set for the modality. The one-hot vectors 510 are then projected into a lower dimensional embedding space of size 1×E that contains a continuous numerical representation of the input variable, rather than a binary value. In the example shown in FIG. 5, E=10, though it should be appreciated that E may be set to any other suitable value and embodiments are not limited in this respect.

In some embodiments, data embedding is accomplished by transforming the one-hot vectors corresponding to each modality element with an embedding matrix 520 of dimensions V×E to produce a plurality of embedding vectors 530, each of which corresponds to a different one of the input data elements (e.g., Gene A in the example of FIG. 5). In some embodiments, the values of embedding matrix 520 are randomly initialized from a uniform distribution with range of −1/V and +1/V. During training of the statistical model the values for parameters of embedding matrix 520 may remain fixed or alternatively may be updated as part of the training process. By updating the parameter values for embedding matrix 520 during training, it is expected that the embedding vectors 530 for connected nodes in the heterogeneous network will be closer in the embedded representation space than non-connected nodes.

Figure 6:
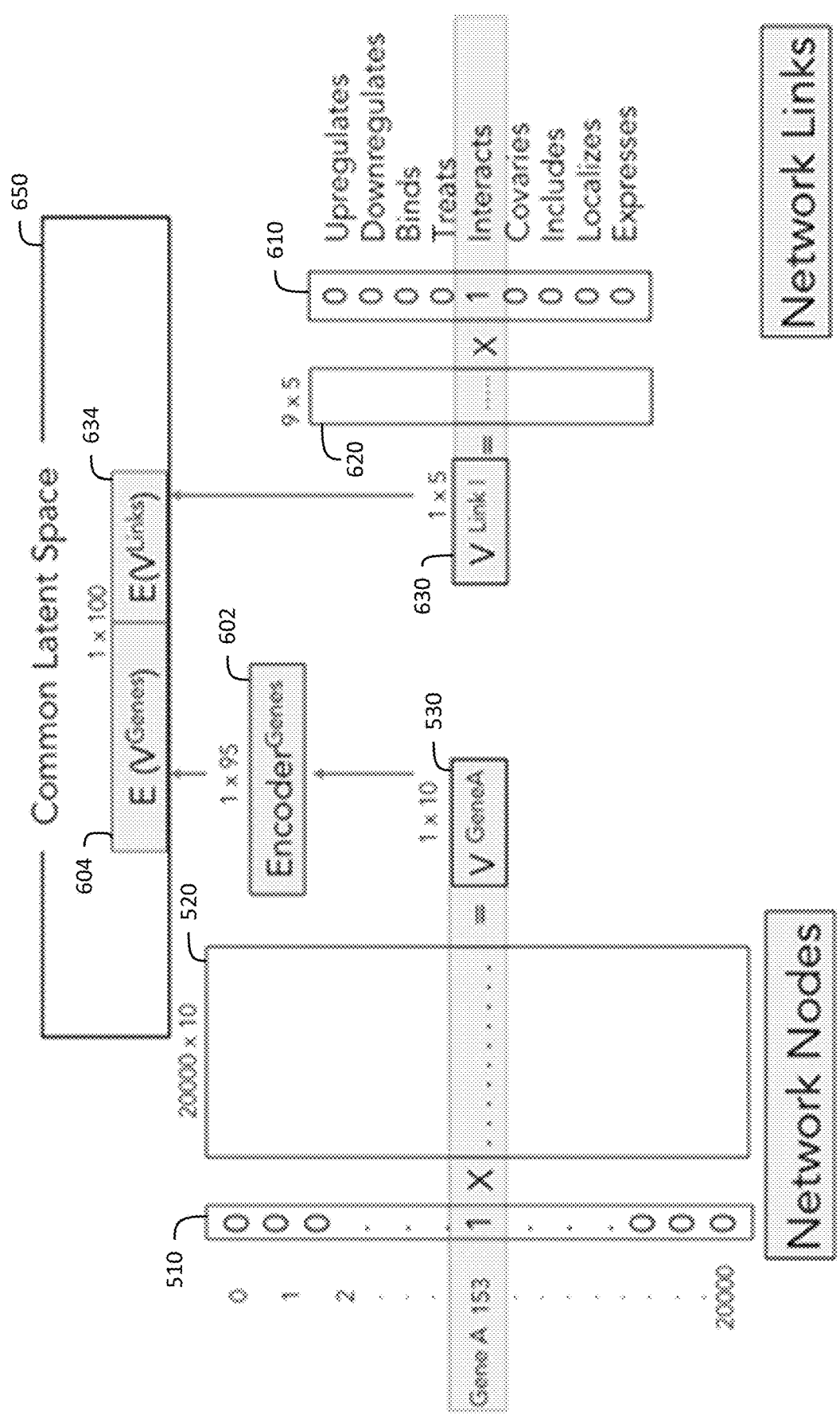
FIG. 6 is a diagram of a process for projecting single-modality information and network links into a common latent space in accordance with some embodiments.

In some embodiments, network links between the nodes in the heterogeneous network are also embedded using a similar embedding procedure as described above, but may have a lower embedding dimension (e.g., 1×5) compared to the dimension of the embedding vectors 530. FIG. 6 schematically illustrates an example of how network links may be encoded in some embodiments. In particular, FIG. 6 illustrates how embedding vectors 530 produced as output of the data embedding architecture described in connection with FIG. 5 are projected into a common latent space 650 using an encoder 602. Common latent space 650 is also referred to herein as a joint-modality representation. As shown, encoder 602 maps each embedding vector 530 to a higher-dimensional latent representation vector 604 within the common latent space 650. In the example of FIG. 6, encoder 602 maps each of the embedding vectors from a dimensionality of 1×10 to a dimensionality of 1×95 in the common latent space 650. It should be appreciated however, that the output dimensionality of encoder 602 may take any suitable value. An example architecture for encoder 602 is described in more detail below in connection with FIG. 7.

FIG. 6 also illustrates that information about the network links is also projected into the common latent space 650 in accordance with some embodiments. In an embedding process similar to that discussed in accordance with FIG. 5, information about network links in a heterogeneous network may be embedded by creating one-hot vectors 610 corresponding to each network link element for a particular node in the network. FIG. 6 shows an example of embedding network links for the "gene" node in the heterogeneous network shown in FIG. 2. One-hot vector 610 includes nine elements, each of which represents one of the nine types of intra-modality or inter-modality network links associated with the "gene" node in FIG. 2. As shown, a one-hot vector with the fifth element being set to 1 and all of the other elements set to 0 may be used, for example, to embed the "interacts" link corresponding to the "gene-interacts-gene" network link. The dimension I of the one-hot vector 610 is based on the number of types of network links associated with each node in the network.

Each of the one-hot vectors may be mapped using an embedding matrix 620 of dimensions I×F to produce a plurality of embedding interaction vectors 630, each of which corresponds to one of the input data elements. As described above, in some embodiments F<E such that the dimensionality of the embedding interaction vectors 630 is less than the dimensionality of the embedding vectors 530. In some embodiments, the values of embedding matrix 620 are randomly initialized from a uniform distribution with range of −1/I and +1/I. During training of the statistical model the values for parameters of embedding matrix 620 may remain fixed or alternatively may be updated as part of the training process. In the example architecture of FIG. 6, the information about network links is represented in the common latent space 650 by concatenating a latent representation vector 604 and an embedding interaction vector 634 output from the network link embedding process, where the concatenated vector in the common latent space 650 represents both modality-specific data and network link information for the modality-specific data.

As described above, some embodiments employ a self-supervised learning technique using pairs of encoders/decoders for each modality or node included in the network. In the self-supervised learning technique, a deep neural network is trained to learn or reproduce an input X based on the reconstruction error between X and the output X'. Training the parameters of the encoders enables the encoders to reconstruct higher-level representations of input vectors, whereas training the decoders enables the decoders to recover the input vectors from higher-level representations.

As described in connection with the architecture of FIG. 6, the inputs of the encoders are the embedding vectors 530 of network nodes, for each variable or element of each modality. The encoders map each embedding vector into a higher dimensional latent representation 604. In some embodiments, the encoders can be characterized by $$Z = \alpha(W_e X + b_e) \quad \text{(Equation 1)}$$

where X is the embedding input vector 530, Z is the output vector or latent representation 604, $W_e$ and $b_e$ represent linear weights and bias, respectively, and a is an activation function. In some embodiments, the activation function is a non-linear activation function, for example, a Rectified Linear Unit (ReLU), Exponential Linear Unit (ELU) or leaky ReLu activation function.

Figure 7:
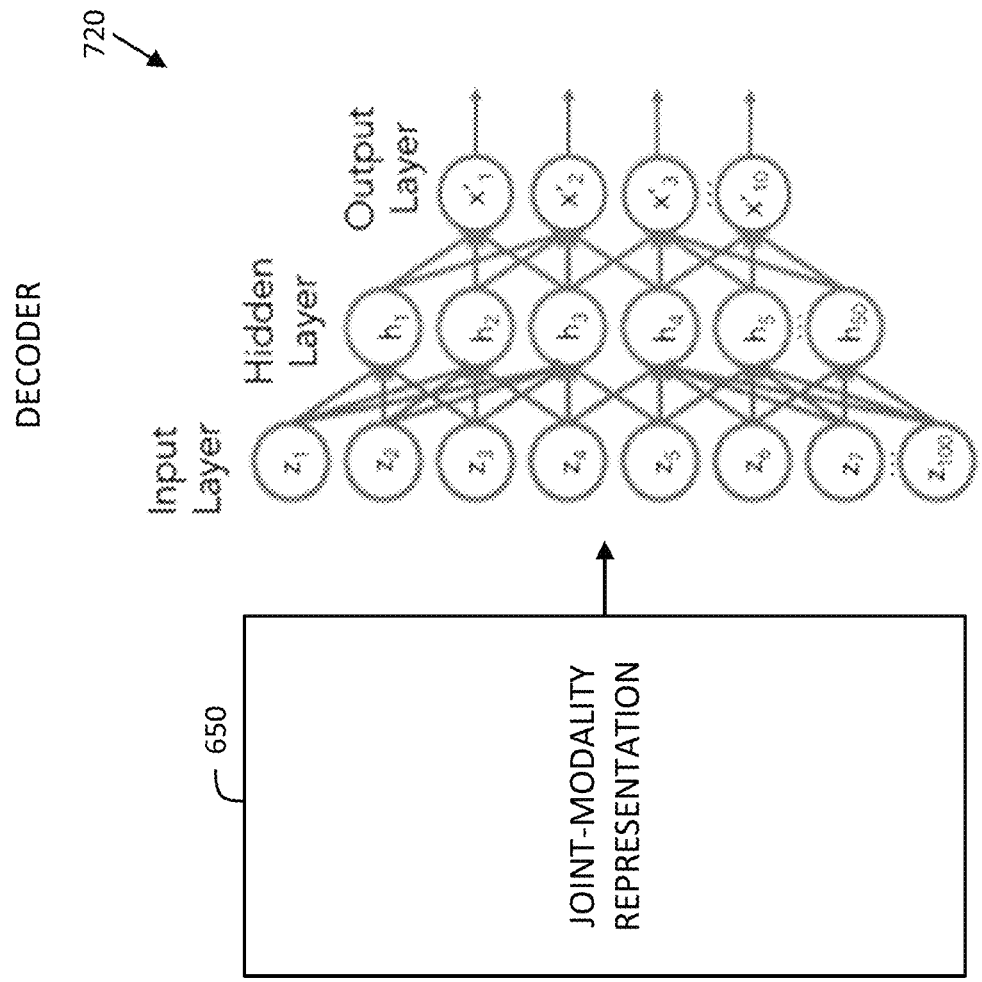
FIG. 7 shows example neural network architectures for encoders and decoders used in accordance with some embodiments.
Figure 7:
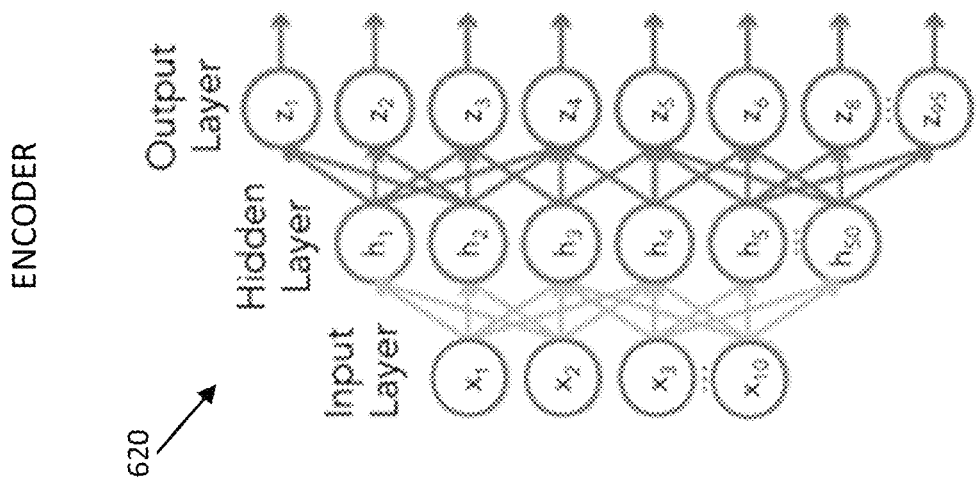

FIG. 7 illustrates an example architecture for an encoder 620 that may be used in accordance with some embodiments. In the example shown in FIG. 7, encoder 620 is implemented as a fully connected neural network with one hidden layer, and dimensions 10 (input layer)→50 (hidden layer)→95 (output layer). The output layer of the encoder 620 is a joint representation vector in the common latent space 650.

The decoder portion of each encoder/decoder pair is configured to map the latent or joint representation of two interacting nodes (Z) in the heterogeneous network back to the embedding representation vector of input variables or individual network nodes (X'). In some embodiments, decoders can be characterized by $$X' = \alpha(W_d Z + b_d) \quad \text{(Equation 2)}$$

where $W_d$ and $b_d$ represent linear weights and bias, respectively, and a is an activation function. In some embodiments, the activation function is a non-linear activation function, for example, a Rectified Linear Unit (ReLU), Exponential Linear Unit (ELU) or leaky ReLu activation function.

FIG. 7 also illustrates an example architecture for a decoder 720 that may be used in accordance with some embodiments. In the example shown in FIG. 7, decoder 620 is implemented as a fully connected neural network with one hidden layer, and dimensions 100 (input layer)→50 (hidden layer)→10 (output layer). The output layer of the decoder 720 is a decoded vector X' having the same dimensionality as the embedding vector X provided as input to the encoder 620.

Having discussed a general architecture for components of a multi-modal statistical model that may be used to represent a heterogeneous network of biological data, examples of training the multi-modal statistical model to learn the associations between data in nodes of the network are provided below.

Figure 8:
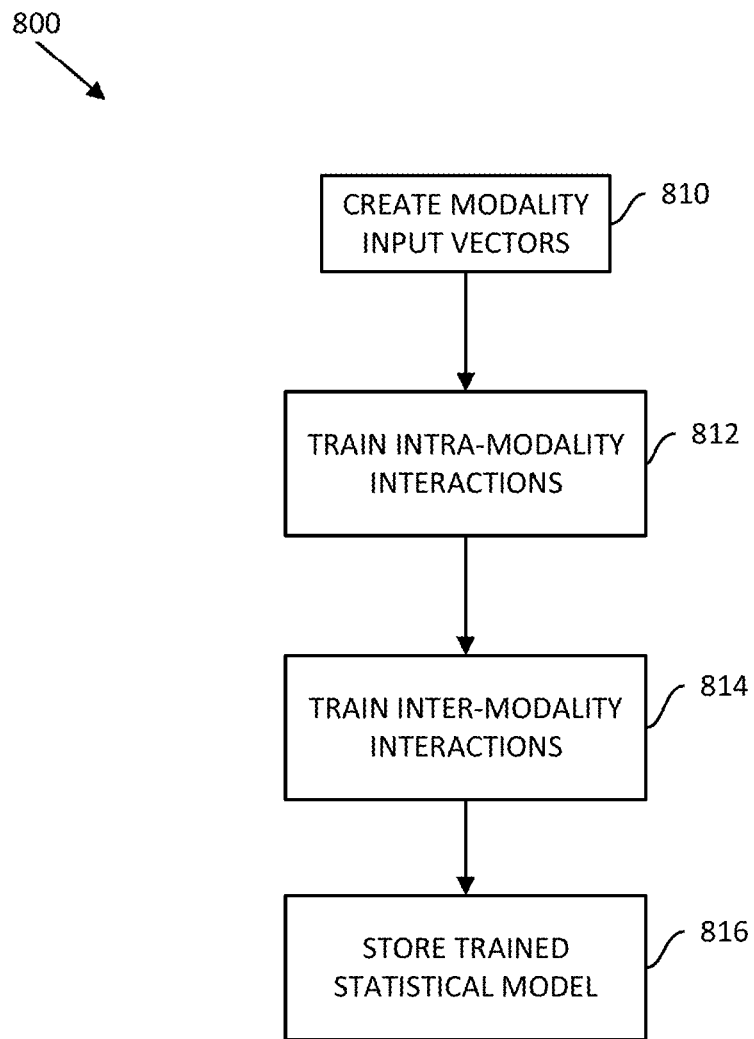
FIG. 8 is a flowchart of a process for training a statistical model to represent intra- and inter-modality network links in a heterogeneous network in accordance with some embodiments.

FIG. 8 shows a flowchart of a process 800 for training a multi-modal statistical model in accordance with some embodiments. The particular training techniques used may depend on the types of interactions between the data in the nodes of the heterogeneous network that are to be represented in the model. In act 810, the modality-specific embedding vectors are created using the data embedding processes described above. In embodiments that also create embedding interaction vectors for concatenation in the common latent space, such embedding interaction vectors may also be created in act 810 using the embedding techniques described herein.

Process 800 then proceeds to act 812, where the multi-modal statistical model is trained to learn intra-modality interactions for each of the nodes in the heterogeneous network that includes at least one intra-modality interaction. For example, in the heterogeneous network shown in FIG. 2, only the "gene" and "drug" nodes are associated with intra-modality links. Accordingly, for each of these nodes, the multi-modal statistical model may be separately trained to learn the corresponding intra-modality network links for the node. An example of training the multi-modal statistical model to learn intra-modality network links is described in more detail below in connection with FIG. 9. It should be appreciated that some heterogeneous networks may not include any nodes associated with intra-modality links and that, for such network, training intra-modality links in act 812 may be omitted.

Process 800 then proceeds to act 814, where the multi-modal statistical model is trained to learn inter-modality interactions describing relationships between data in different connected nodes in the heterogeneous network. As described above, each of the nodes in the heterogeneous network is connected to at least one other node in the network via one or more inter-modality network links. For each of these network links, training in act 814 is repeated until the multi-modal statistical model has been trained on all of the network links in the heterogeneous network. An example of training the multi-modal statistical model to learn inter-modality links is described in more detail below in connection with FIGS. 10A-C. Although act 814 is illustrated following act 812, it should be appreciated that training of intra-modality links and inter-modality links may be performed for the nodes of the heterogeneous network in any suitable order including, but not limited to, training on all intra-modality links before training on inter-modality links, training on all inter-modality links before training on intra-modality links, and interspersing the training of intra-modality and inter-modality links.

Process 800 then proceeds to act 816, where parameters for the trained statistical model estimated during training are stored for use in performing prediction tasks. Although act 816 is shown following acts 812 and 814, it should be appreciated that estimated parameters for the trained statistical model may be stored after one or more training iterations in acts 812 or 814 such that the estimated parameters determined in one training iteration are used to initialize at least some of the parameters of the model for a subsequent training iteration. As an example, a first training iteration may be focused on training the "gene-interacts-gene" network link with the result of the training being a gene encoder and a gene decoder with estimated parameters that reflect this intra-modality interaction. The estimated parameters for the gene encoder and gene decoder may be stored and used to initialize model parameters for a subsequent training iteration focused on training the "drug-binds-gene" network link. During the subsequent training interaction the estimated parameters for the gene encoder/decoder are further refined from the previously-stored values to reflect associations associated with inter-modality training. Examples of propagation of estimated model parameters from one training iteration to a subsequent training iteration are discussed in more detail below.

Figure 9:
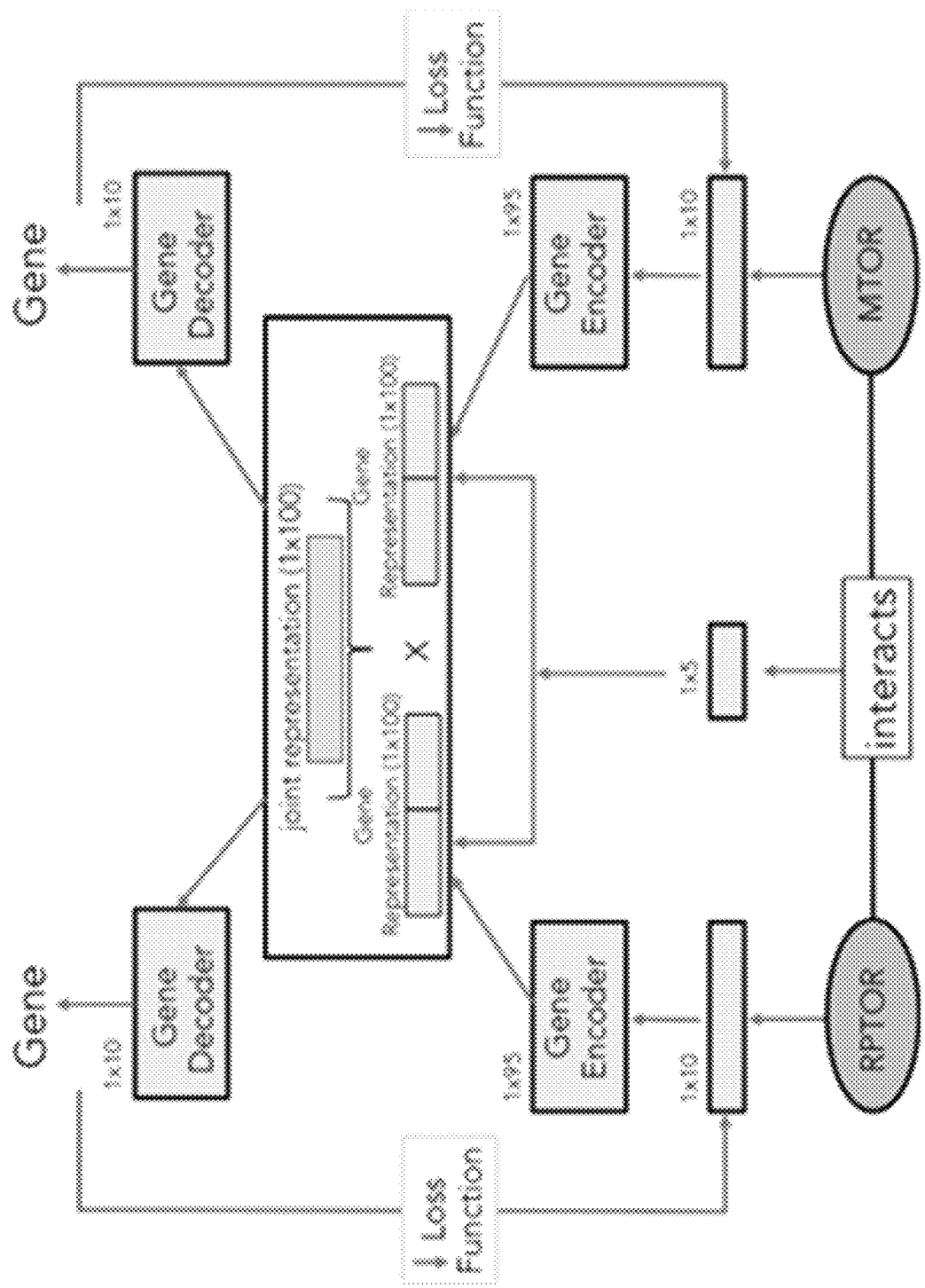
FIG. 9 is a diagram of a process for training a statistical model to represent intra-modality network links in accordance with some embodiments.

FIG. 9 schematically illustrates a process for training a multi-modal statistical model to learn the network link "gene-interacts-gene" in accordance with some embodiments. As shown in FIG. 9, two gene encoder/decoder pairs are shown as being simultaneously trained. Although shown as two separate networks for purpose of illustration, it should be noted that each of the gene encoder pair and the gene decoder pair illustrated in FIG. 9 correspond to a single network structure, examples of which are shown in FIG. 7. The single network structure for the gene encoder and the gene decoder include parameters (e.g., network weights) that are estimated and updated during training using the self-supervised learning techniques described herein.

As shown, coupling the outputs of the encoders and inputs of the decoders is a joint representation, which represents the intra-modality network links on which the multi-modal statistical model is trained. FIG. 9 shows training of a network link that encodes an interaction between a first gene RPTOR and a second gene MTOR based on data sourced, for example, from at least one of the data sources listed in Table 1. Each of the genes RPTOR and MTOR is represented in the model as embedding vectors (e.g., having dimension 1×10) using the data embedding techniques described above. Optionally, the network link ("interacts" in the example of FIG. 9) to be trained for the gene-gene pair is also represented as an embedded interaction vector (e.g., having dimension 1×5) as described above.

The embedding vectors for RPTOR and MTOR are provided as input to the instances of the gene encoder, which encode the embedding vector representation for each gene into a corresponding intra-modality representation vector (e.g., having dimension 1×95) in the common latent space. In embodiments in which the network link is also represented as an embedding interaction vector, the intra-modality representation vectors for the "connected" input data (i.e., the data for genes RPTOR and MTOR in FIG. 9) may be concatenated with the embedding interaction vector in the common latent space as shown, resulting in two concatenated vectors (e.g., having dimensions 1×100).

A joint representation vector representing the connected input data and the network link characterizing the connection is computed based on the two intra-modality representation vectors (optionally concatenated with the network link information) in the common latent space. For example, in some embodiments, the joint representation vector is computed by calculating the average or product of the two intra-modality representation vectors in the common latent space. In this implementation the joint representation vector has the same dimension as the concatenated vectors (i.e., 1×100 in the example of FIG. 9). As an alternative to the procedure shown in FIG. 9 for computing a joint representation vector, the joint representation vector may be computed in some embodiments based on a combination of the two intra-modality representation vectors (e.g., using averaging or a product) prior to concatenation with the embedding interaction vector describing the network link, and the embedding interaction vector may be concatenated with the joint representation vector following its creation. In such a scenario the joint representation vector may initially have a dimension the same as the individual intra-modality representation vectors (e.g., 1×95), with the final dimension of the joint representation vector being larger (e.g., 1×100) following concatenation.

The training process in FIG. 9 proceeds by providing the joint representation vector (e.g., having dimension 1×100) as input to the gene decoder (represented in FIG. 9 as two gene decoders for illustration), which is configured to output decoded vectors (e.g., having dimension 1×10) for each of the input genes RPTOR and MTOR. A deviation between the decoded vectors output from the decoders and the embedding input vectors provided as input to the encoders is measured and used to update the weights in the statistical model such that the model learns the associations between the data in a self-supervised way. In some embodiments, the self-supervised learning technique is implemented using a negative sampling loss function, and the error determined from the negative sampling loss function is backpropagated through the encoders and decoders (and optionally the embedding matrices used for data embedding) to update the estimates of the parameters (e.g., weights) for each of these components of the model.

The negative sampling loss function enforces the encoder/decoder pairs to segregate real from random network connections in accordance with the relation below

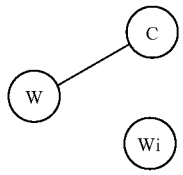

$$\log \sigma(c * w) + \sum_{i=1}^{K} \mathbb{E}_{w_i \sim p(w)}[\log \sigma - (w_i * w)]$$

where w and c represent the connected network nodes, and wi represents an unrelated network node.

When the network link being encoded is an intra-modality network link, as is the case in the example of FIG. 9, errors determined based on both input/output pairs are considered when determining how to update the estimates of the parameters for the single modality encoder representation. Stated differently, the parameters of both of the gene encoder/decoder instantiations illustrated in FIG. 9 would be updated in the same way for each backpropagation cycle.

As discussed briefly above, some embodiments first train the statistical model to learn the intra-modality network links followed by training on the inter-modality network links. In the case of network nodes already encoded in a previous training iteration, the parameters stored for the pre-trained representations of the network components (e.g., encoders, decoders, embedding matrices) may be used in subsequent training iterations using different inputs.

Figure 10A:
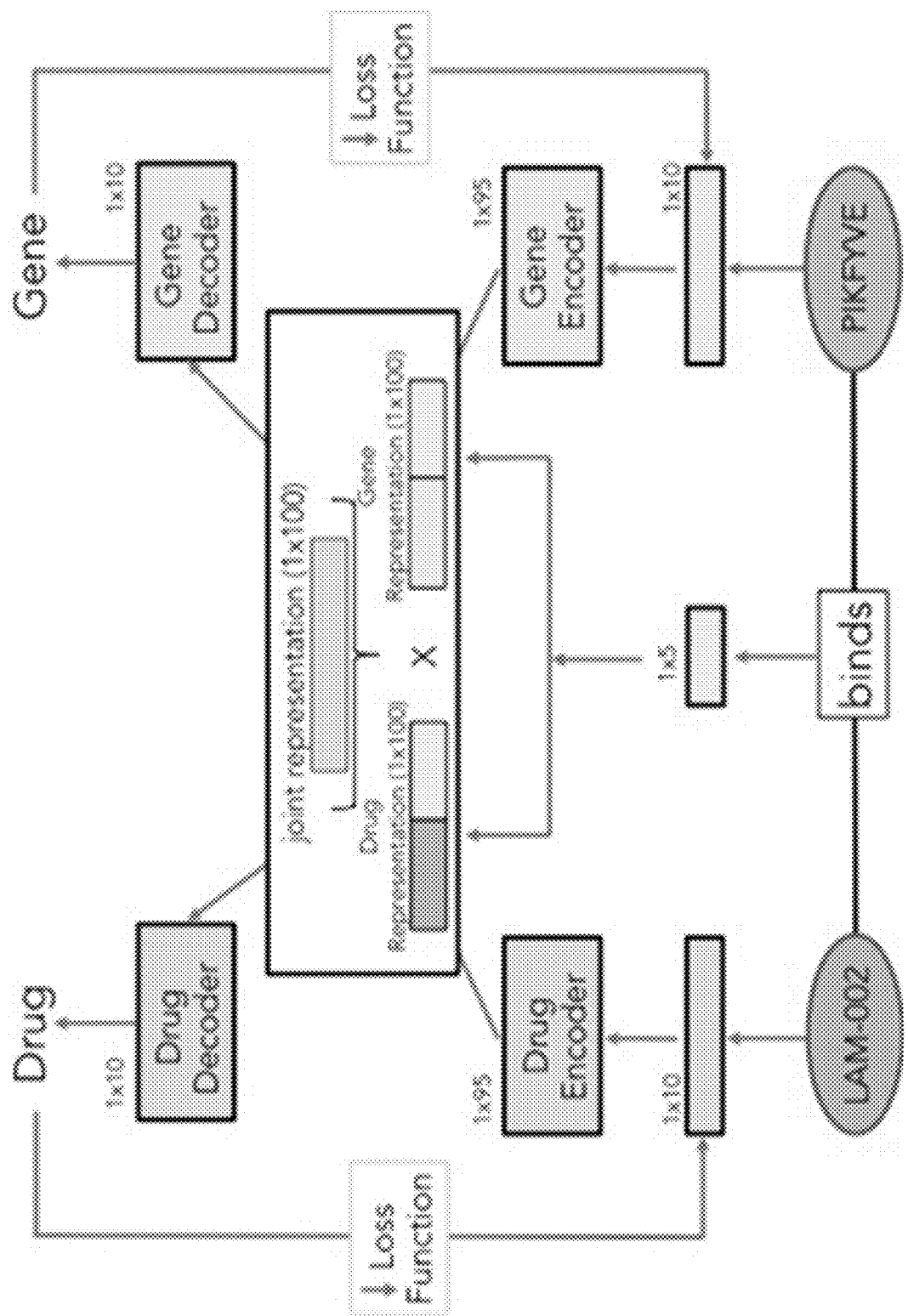
FIGS. 10A-10C are diagrams of processes for training a statistical model to represent inter-modality network links in accordance with some embodiments.

FIG. 10A shows an example for training a multi-modal statistical model to learn an inter-modality interaction for a heterogeneous network in accordance with some embodiments. In particular, FIG. 10A shows how the statistical model may be trained to learn the "drug-binds-gene" network link in the heterogeneous network shown in FIG. 2. The training process outlined in FIG. 10A is similar to that described in FIG. 9 for training an intra-modality network interaction, with the primary differences being the inputs and the encoders/decoders used for the training. Briefly, embedding vectors are created for specific data pairs from different modalities (drugs and genes in the example of FIG. 10A) corresponding to different nodes in the heterogeneous network. The embedding vectors are created using the data embedding processes described above using one-hot vectors and corresponding embedding matrices. In the example shown in FIG. 10A, a first embedding vector is created for the drug LAM-002 and a second embedding vector is created for the gene PIKFYVE. The embedding vectors are provided as input to respective drug and gene encoders to map each of the embedding vectors into a higher-dimensional modality-specific latent representation in the common latent representation space. The architecture of the drug and gene encoders may be similar to those described above in connection with FIG. 7. In some embodiments, the encoder/decoder architecture may have different architectures for different modalities by, for example, having a different number of hidden layers and/or layers with a different dimensionality, with the output representation having the same dimensionality (e.g., 1×95) for each of the encoders/decoders. In other embodiments, the architecture for the encoders/decoders is identical for each modality of data represented in the statistical model, with the differences between the encoders/decoders being reflected in the weights represented in the networks.

As discussed briefly above, one or both of the encoder/decoder pairs may be associated with parameter values that are initialized based on at least one prior training iteration. For example, in a scenario in which the intra-modality training of a gene encoder/decoder as shown in FIG. 9 was performed prior to the inter-modality training of drug and gene encoders/decoders as shown in FIG. 10A, the pretrained gene encoder/decoder pair resulting from the training in FIG. 9 may be used to initialize the parameters of the gene encoder/decoder pair in the architecture of FIG. 10A. In this way the encoder/decoder pair for each modality continues to be trained as new pairs of data and network interactions are provided as input to the multi-modal statistical model.

As shown in FIG. 10A, the modality-specific latent representations output from the encoders may be concatenated to an embedding interaction vector representing a particular inter-modality network link between the input data ("binds" in the example of FIG. 10A). In embodiments in which concatenation is used to incorporate the network link information in the common latent representation, the concatenation may occur when generating the modality-specific latent representations or the concatenation may occur after the modality-specific latent representations have been combined to create a joint representation. The modality-specific latent representations may be combined, for example, by taking an average or product of the two latent representations to compute a joint representation vector that represents the "drug-binds-gene" network interaction for the input data pair of drug LAM-002 and gene PIKFYVE. Continuing with the training, the joint representation is provided as input to both a drug decoder and a gene decoder to produce decoded output vectors (e.g. having dimension 1×10), and the parameters of the encoders and decoders (and optionally the embedding matrices) are updated based on a comparison of the decoded output vectors and the embedding vectors provided as input to the encoders. Examples of how the weights may be updated using backpropagation in accordance with some embodiments are discussed above.

Figure 10B:
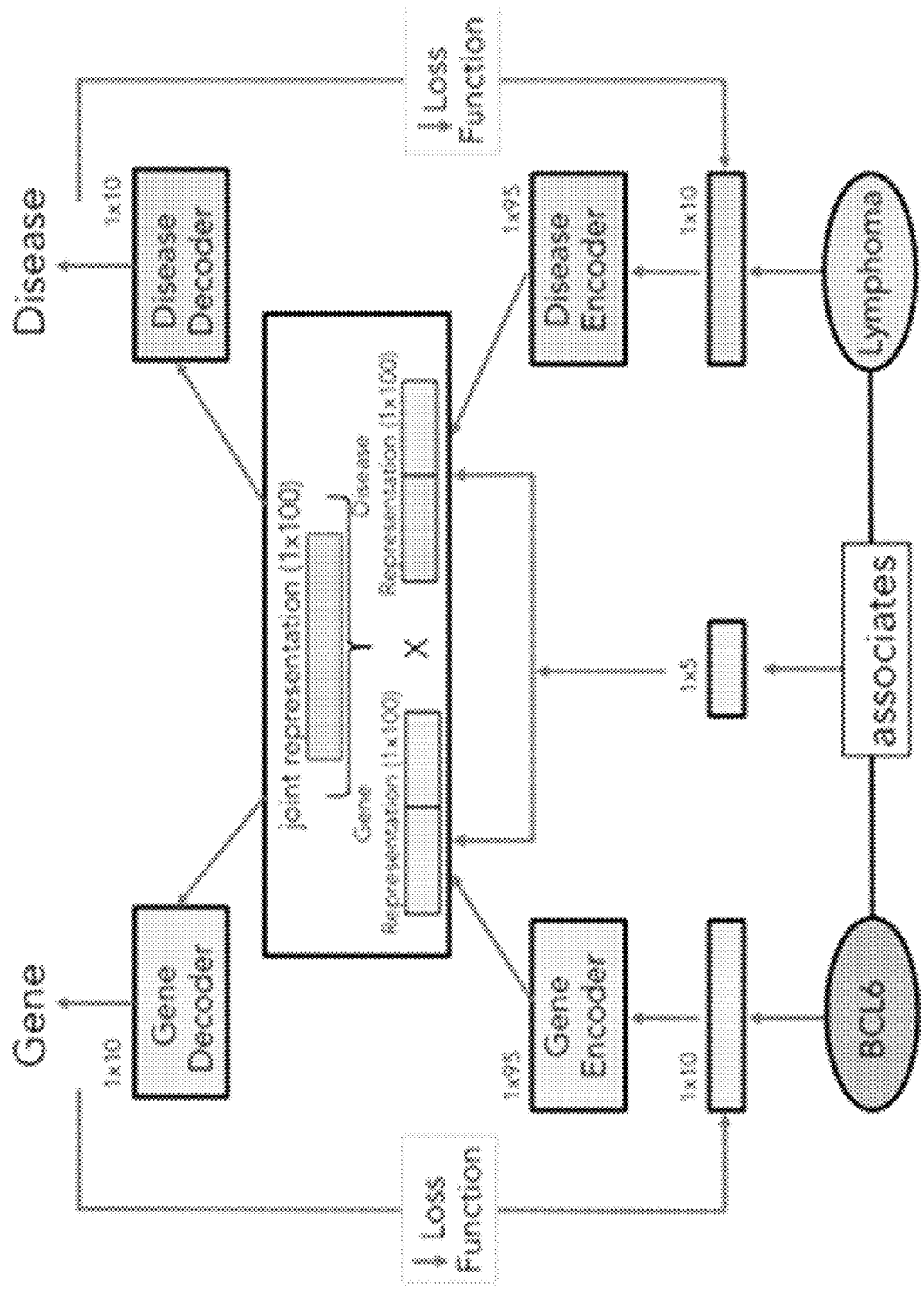

FIG. 10B shows another example for training a multi-modal statistical model to learn inter-modality interactions for a heterogeneous network in accordance with some embodiments. In particular, FIG. 10B shows how the statistical model may be trained to learn the "disease-associates-gene" network link in the heterogeneous network shown in FIG. 2. The training process outlined in FIG. 10B is similar to that described in FIG. 10A, with the primary differences being the inputs and the encoders/decoders used for the training. Briefly, embedding vectors are created for specific data pairs from different modalities (genes and diseases in the example of FIG. 10B) corresponding to different nodes in the heterogeneous network. The embedding vectors are created using the data embedding processes described above using one-hot vectors and corresponding embedding matrices. In the example shown in FIG. 10B, a first embedding vector is created for the gene BCL6 and a second embedding vector is created for the disease Lymphoma. The embedding vectors are provided as input to respective gene and disease encoders to map each of the embedding vectors into a higher-dimensional modality-specific latent representation in the common latent representation.

One or both of the encoder/decoder pairs may be associated with parameter values that are initialized based on at least one prior training iteration. For example, in a scenario in which the inter-modality training of a gene encoder/decoder as shown in FIG. 10A was performed prior to the inter-modality training of gene and disease encoders/decoders in FIG. 10B, the pre-trained gene encoder resulting from the training in FIG. 10A may be used to initialize the parameters of the gene encoder and decoder in the architecture of FIG. 10B. In this way the encoder/decoder pair for each modality continues to be trained as new pairs of data and network interactions are provided as input to the multi-modal statistical model.

As shown in FIG. 10B, the modality-specific latent representations output from the encoders may be concatenated to an embedding interaction vector representing a particular inter-modal network link between the input data ("associates" in the example of FIG. 10B). In embodiments in which concatenation is used to incorporate the network link information in the common latent representation, the concatenation may occur when generating the modality-specific latent representations or the concatenation may happen after the modality-specific latent representations have been combined to create a joint representation. The modality-specific latent representations may be combined, for example, by taking an average or product of the two representations to compute a joint representation vector that represents the "disease-associates-gene" network interaction for the input data pair of gene BCL6 and disease Lymphoma. Continuing with the training, the joint representation is provided as input to both a gene decoder and a disease decoder to produce decoded output vectors (e.g. having dimension 1×10), and the parameters of the encoders and decoders (and optionally the embedding matrices) are updated based on a comparison of the decoded output vectors and the embedding vectors provided as input to the encoders. Examples of how the weights may be updated using backpropagation in accordance with some embodiments are discussed above.

Figure 10C:
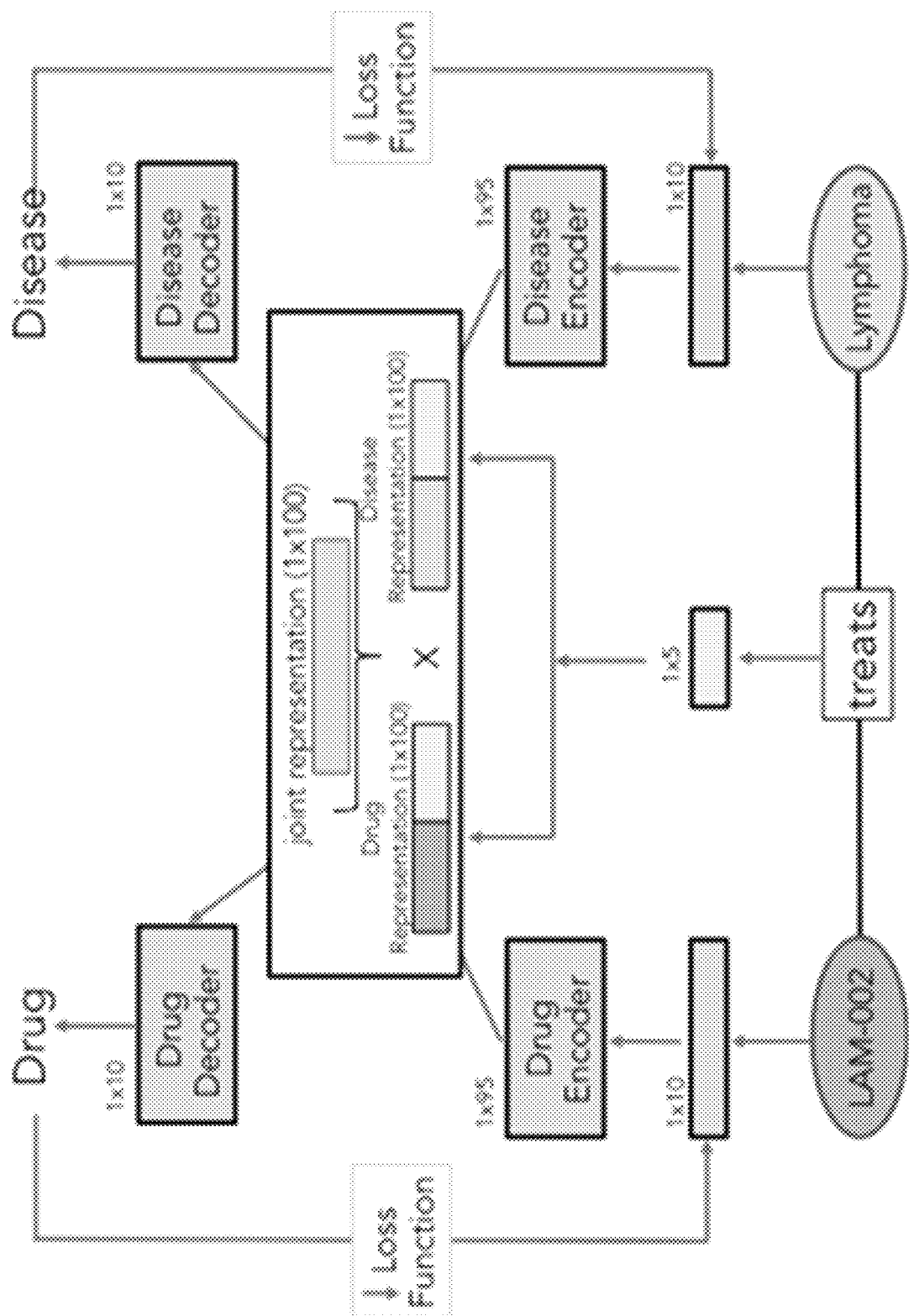

FIG. 10C shows another example for training a multi-modal statistical model to learn inter-modality interactions for a heterogeneous network in accordance with some embodiments. In particular, FIG. 10C shows how the statistical model may be trained to learn the "drug-treats-disease" network link in the heterogeneous network shown in FIG. 2. The training process outlined in FIG. 10C is similar to that described in FIGS. 10A and 10B, with the primary differences being the inputs and the encoders/decoders used for the training. Briefly, embedding vectors are created for specific data pairs from different modalities (drugs and diseases in the example of FIG. 10C) corresponding to different nodes in the heterogeneous network. The embedding vectors are created using the data embedding processes described above using one-hot vectors and corresponding embedding matrices. In the example shown in FIG. 10C, a first embedding vector is created for the drug LAM-002 and a second embedding vector is created for the disease Lymphoma. The embedding vectors are provided as input to respective drug and disease encoders to map each of the embedding vectors into a higher-dimensional modality-specific latent representation in the common latent representation.

One or both of the encoder/decoder pairs may be associated with parameter values that are initialized based on at least one prior training iteration. For example, in a scenario in which the inter-modality training of a drug encoder/decoder as shown in FIG. 10A and the inter-modality training of a disease encoder/decoder in FIG. 10B was performed prior to the inter-modality training shown in FIG. 10C, the pre-trained drug encoder/decoder pair resulting from the training in FIG. 10A may be used to initialize the parameters of the drug encoder/decoder pair in the architecture of FIG. 10C and the pre-trained disease encoder/decoder pair resulting from the training in FIG. 10B may be used to initialize the parameters for the disease encoder/decoder pair in the architecture of FIG. 10C. In this way the encoder/decoder pair for each modality continues to be trained as new pairs of data and network interactions are provided as input to the multi-modal statistical model.

As shown in FIG. 10C, the modality-specific latent representations output from the encoders may be concatenated to an embedding interaction vector representing a particular inter-modal network link between the input data ("treats" in the example of FIG. 10C). In embodiments in which concatenation is used to incorporate the network link information in the common latent representation, the concatenation may occur when generating the modality-specific latent representations or the concatenation may happen after the modality-specific latent representations have been combined to create a joint representation vector. The modality-specific latent representations may be combined, for example, by taking an average or product of the two representations to compute a joint representation vector that represents the "drug-treats-disease" network interaction for the input data pair of drug LAM-002 and disease Lymphoma. Continuing with the training, the joint representation vector is provided as input to both a drug decoder and a disease decoder to produce decoded output vectors (e.g. having dimension 1×10), and the parameters of the encoders and decoders (and optionally the embedding matrices) are updated based on a comparison of the decoded output vectors and the embedding vectors provided as input to the encoders. Examples of how the weights may be updated using backpropagation in accordance with some embodiments are discussed above.

All of the examples provided above in FIGS. 9 and 10A-C relate to training the statistical model to learn network interactions in the heterogeneous network of FIG. 2 that are categorical only. As discussed above, some network interactions may be both represented by both categorical and numerical features, wherein the numerical features represent a strength of an interaction between data within or among nodes in the network. For training the multi-modal statistical modal to learn network links that are both categorical and numerical, the numerical information may be used to scale the representation vectors represented in the joint-modality representation. For example, the embedding interaction vectors concatenated to the joint representation vectors may be scaled by the numerical information.

Various parameters (e.g., hyperparameters) of the multi-modal statistical architecture may be modified based on optimization for a particular implementation. Such parameters include but, are not limited to, embedding dimension (example, 1×10), joint representation dimension (example, 1×100), dimension of hidden layer(s) of encoders and decoder (example, 1×50), number of hidden layers of encoders and decoders (example, 1), activation function for the encoders and decoders, and the learning rate.

Figure 11:
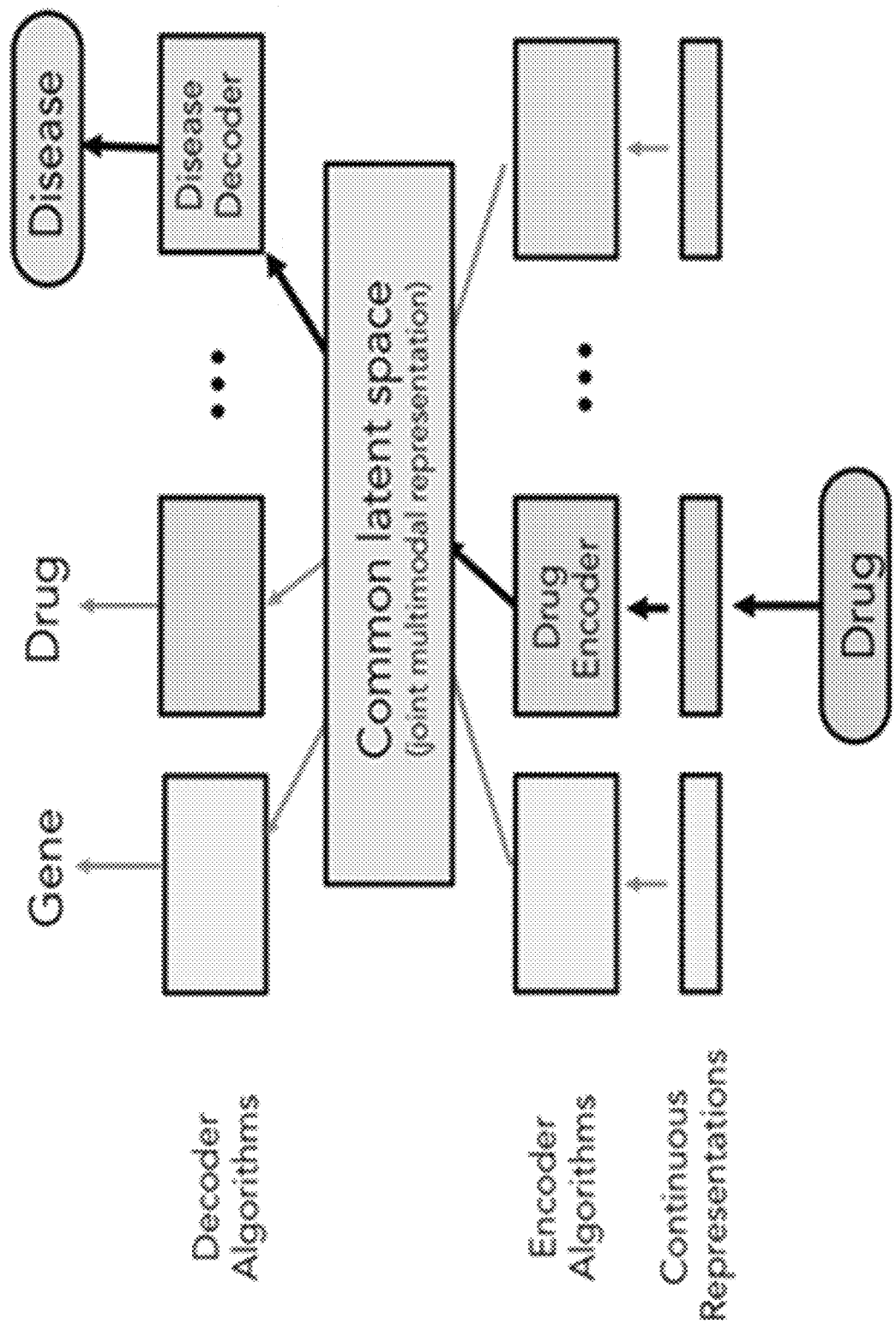
FIG. 11 schematically illustrates making a multi-modal prediction using a trained multi-modal statistical model in accordance with some embodiments.

As discussed in connection with FIG. 3, the overall architecture of the multi-modal statistical model once trained includes a plurality of trained modality-specific encoders and decoders and a joint-modality representation that couples the trained encoders to the trained decoders. As shown schematically in FIG. 11, the trained multi-modal statistical model may be used to make predictions between input data having a first modality and an output having a different modality through the selection of an appropriate pair of trained encoders and decoders used for the prediction. Specifically, FIG. 11 shows the ability of the trained multi-modal statistical model to make predictions about diseases that are likely be treatable by a particular drug. The prediction is made, in part, by using a trained drug encoder and a trained disease decoder, as shown. Multiple types of predictions can be made using the trained multi-modal statistical network, including, but not limited to, new disease indications for a given drug, candidate drugs and combination therapies for a given disease or patient, biomarkers associated with a disease, and potential gene targets for a given drug. Making such predictions is not possible using conventional techniques for modeling biological data that consider only one or two modalities of data.

Figure 12:
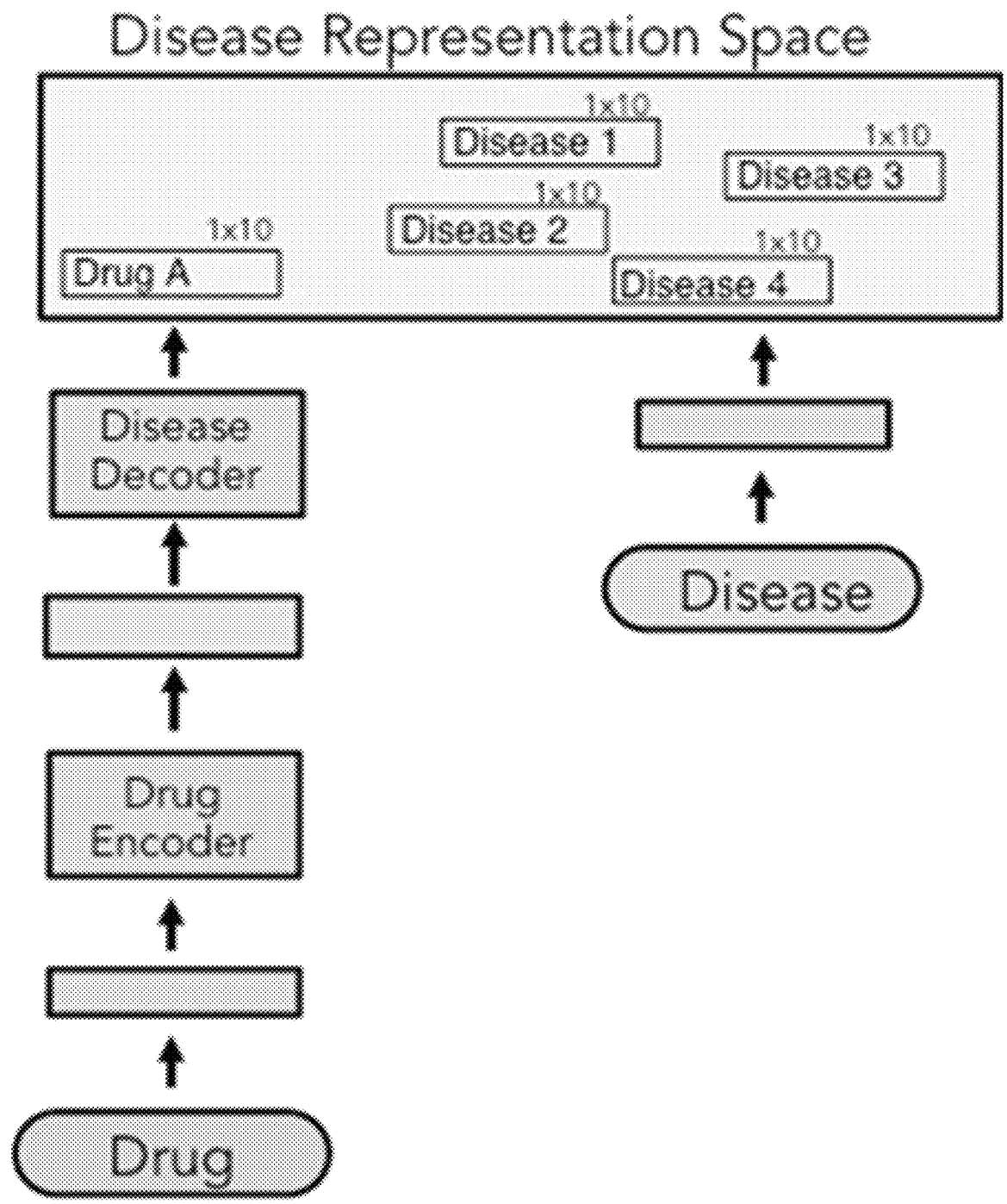
FIG. 12 shows a process for making unsupervised predictions in a modality-specific representation space in accordance with some embodiments.

Some embodiments are directed to unsupervised prediction techniques using a trained multi-modal statistical model. FIG. 12 shows an example of an unsupervised prediction technique in which the representation space for a first modality (drug in the example of FIG. 12) is mapped onto the representation space for a second modality (disease in the example of FIG. 12) using a decoder for the second modality. In the prediction technique shown in FIG. 12, candidate disease indications are predicted for a given drug provided as input to the trained statistical model. The trained drug encoder is used to compute a latent representation vector for the drug of interest in the joint-modality representation, and the latent representation vector is provided as input to the trained disease decoder. The output of the trained disease decoder is a representation of the input drug projected into the disease representation space.

Figure 13:
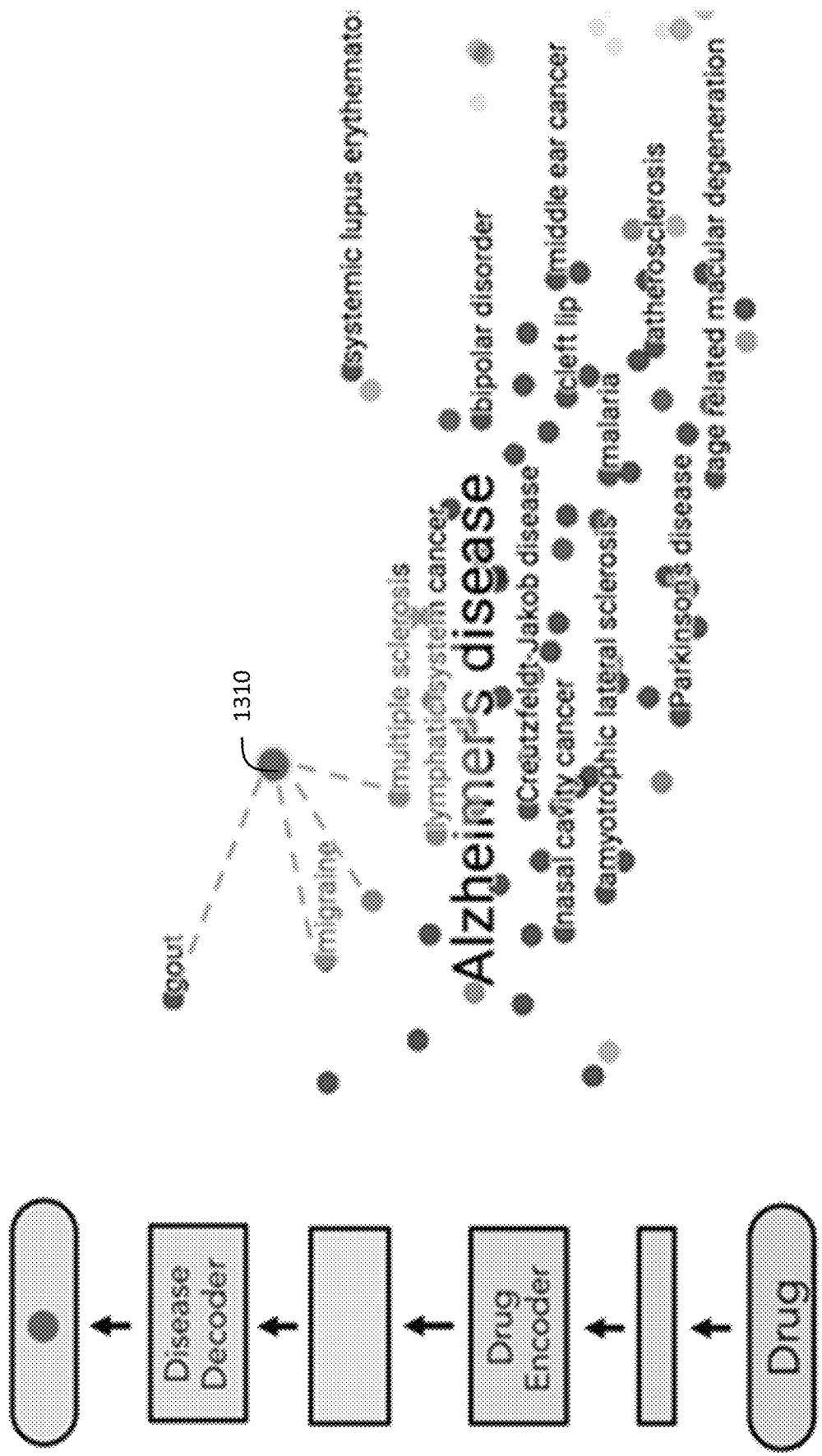
FIG. 13 schematically illustrates a technique for comparing positions of embedding and projected vectors in a modality-specific representation space in accordance with some embodiments.

Rather than mapping the input drug to a particular disease in the disease representation space, the output of the disease decoder may be projected as a point 1310 in the disease representation space, as shown schematically in FIG. 13. The disease representation space shown in FIG. 13 is a t-Distributed Stochastic Neighbor Embedding (t-SNE) representation of the "disease latent space" containing just a subset of the disease database. Each of the diseases on which the multi-modal statistical model was trained also has an intrinsic position in the n-dimensional disease representation space. In some embodiments, a new disease indication is predicted based, at least in part, on a distance between the projected point 1310 and the positions of other diseases in the disease representational space. For example, new disease indications for the drug may be determined by finding nearest neighbors of the projected point 1310 and candidate diseases projected within the disease representation space. Candidate diseases with the highest potential of being treatable by the given drug may include diseases in which the distance between the project point 1310 and the points for the candidate diseases is small. For example, as shown in FIG. 13, the diseases of gout, migraine and multiple sclerosis are each associated with points in the disease representation space closest to the projected point 1310 for a given input drug. As such, these diseases may be good candidates as new disease targets for the drug of interest.

In some embodiments, only the disease having the closest distance to the projected point 1310 may be provided as an output prediction. In other embodiments, an "n-best" list of diseases associated with distances closest to the projected point 1310 may be provided as an output prediction. In yet other embodiments, only diseases having a distance less than a threshold value from the projected point 1310 in the disease representation space may be output. Other information in addition to the disease name(s) may be output including, but not limited to, a similarity score based on the distance.

Any suitable measure of distance between two points in the n-dimensional representation space may be used, and embodiments are not limited in this respect. Examples of distance measurements that can be used in accordance with some embodiments for prediction include, but are not limited to, Euclidean distance, Cosine similarity, and Manhattan distance. A formula for Euclidean distance between two vectors in a common representation space may be as follows:

$$d(p,q) = d(q,p) = \sqrt{(q_1-p_1)^2 + (q_2-p_2)^2 + \ldots + (q_n-p_n)^2}.$$

Figure 14:
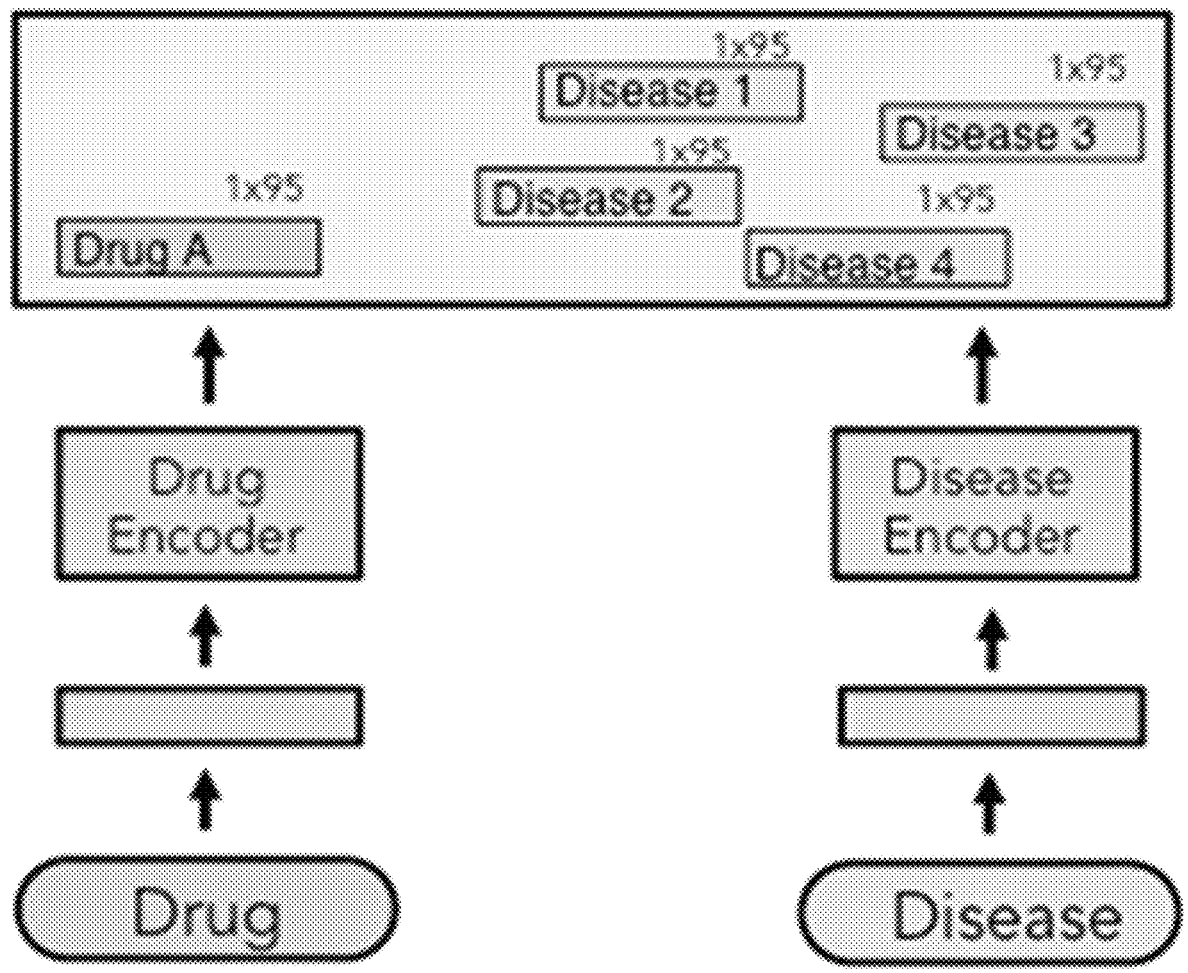
FIG. 14 shows a process for making unsupervised predictions in a joint-modality representation space in accordance with some embodiments.

FIG. 14 shows an example of another unsupervised prediction technique in which input data for two different modalities (drug and disease in the example of FIG. 14) is projected into the joint-modality representation space, where comparisons between the joint representation vectors from the different modalities can be made. As shown, in the prediction technique of FIG. 14, input data for a first modality (drug in the example of FIG. 14) is provided to a trained encoder for the first modality. The output of the trained encoder for the first modality is a first joint representation vector for the first modality input in the common latent space. Additionally, input data for a second modality (a plurality of diseases in the example of FIG. 14) are provided as input to a trained encoder for the second modality. The output of the trained encoder for the second modality is a plurality of second joint representation vectors represented in the common latent space, each of which corresponds to input data for the second modality.

A prediction for candidate disease indications for a given drug may be determined by comparing a distance of the first joint representation vector for the input drug within the common latent space and each of the second joint representation vectors for the projected diseases into the common latent space. For example, in order to predict the association between a drug A and four different diseases, the drug and disease encoders may be used to compute the corresponding latent representations for drug A and each of the four diseases. The distance between the latent representation vectors for drug A and those for each disease projected into the common latent space may be computed to predict the closest disease representation to the representation of drug A. The candidate diseases with the highest potential of being treatable by the given drug may be those diseases having positions in the latent representation space that are closest to the position of the drug of interest in the latent representation space.

Although the unsupervised prediction techniques described in FIGS. 12 and 14 relate to predicting new disease indications for particular drugs, it should be appreciated that unsupervised prediction techniques may be used to make predictions between any two modalities represented in the trained statistical model by selecting appropriate trained encoders and/or decoders to enable the prediction within a common representation space within the multi-modal statistical model.

Figure 15:
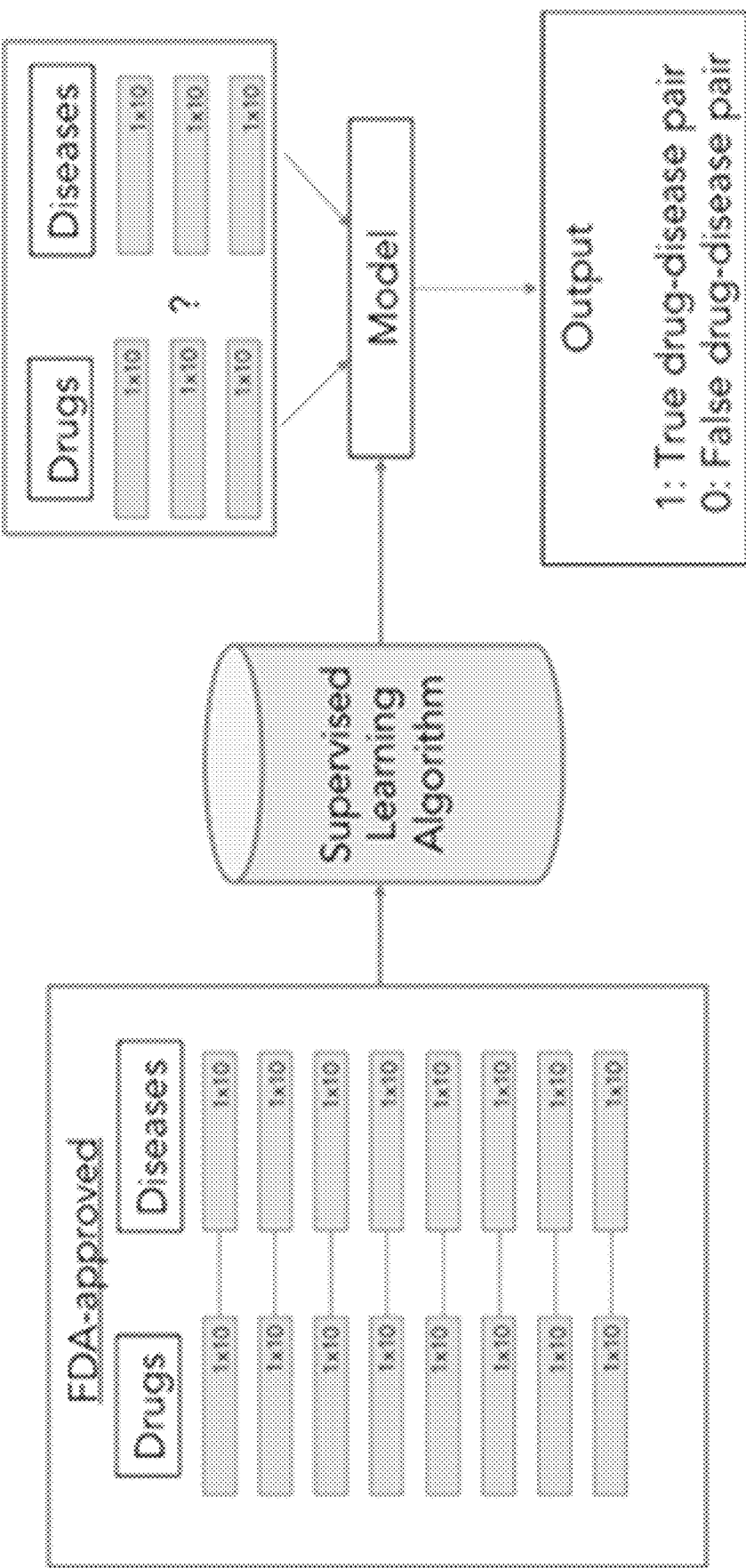
FIG. 15 shows a process for making supervised predictions using a trained multi-modal statistical model in accordance with some embodiments.

Some embodiments are directed to supervised prediction techniques using a trained multi-modal statistical model. FIG. 15 illustrates a supervised prediction technique that uses a supervised classifier trained with known network interactions of two different modalities. The supervised classifier may be implemented using any suitable architecture including, but not limited to, a neural network, a tree-base classifier, other deep learning or machine learning classifiers, or using statistical correlation techniques. The classifier may be trained with the latent representations of the known network interaction pairs (e.g., from approved disease indications for FDA approved drugs), and predictions about whether or not there is a true association given new pair may be made using the trained classifier.

As shown, the supervised classifier in FIG. 15 may be trained with representation vectors of FDA-approved drug-disease pairs. The input vectors for drugs and diseases may have a dimension corresponding to a data embeddings layer (e.g., 1×10) if using the disease decoder to project the drugs to the disease representation space or the drug decoder to project the diseases to the drug representation space, or a dimension of the latent representation space (e.g., 1×95) if using the latent representation of both modalities to make classification decisions using the trained supervised classifier.

In addition to the predication examples described above, other types of predictions are also contemplated by some embodiments. For example, predictions about new drugs that may be effective in treating a given disease may be made. A disease of interest and all drugs may be projected into a common representation space (e.g., a modality-specific representation space or the common latent space) in the multi-modal statistical model and distances between vectors in the common representation space may be used to predict the new drugs for treating the disease.

Because all entities in the heterogeneous network represented in the multi-modal statistical model have representations in the same latent space, and encoders and decoders have been trained to access the latent space, other cross-modality predictions, in addition to new drug-disease matches, can be made. For example, diseases can be encoded by a trained disease encoder to predict gene targets in the common latent space, or by passing the disease latent representation through the gene decoder and comparing the representation directly in the gene space (e.g., through nearest neighbor and other aforementioned distance measurement or similarity techniques). In this manner, in addition to predicting new drugs associated with a given disease, genes, proteins, pathways, anatomies, and other biological entities can be also be associated with the disease, providing context to the drug-disease prediction. Additionally, a specific mutation in the heterogeneous network can be shown to have strong associations with drugs and diseases, thereby indicating biomarkers that could help to identify patients that will respond to given drugs.

In yet another prediction scenario, gene targets of a drug may be predicted in accordance with some embodiments. Drugs are associated with genes, mutations, and other heterogeneous network entities, which may provide mechanistic insights of drug action. This can be valuable, for example, for further fine-tuning of drug-disease predictions based on expert knowledge and traditional drug engineering.

Yet another prediction technique relates to predicting patient-specific therapies. The trained multi-modal statistical model may be used to predict specific drugs/therapies for specific patients. For example, as described above some embodiments are configured to predict biomarkers associated with a given disease. Patients can be screened for these biomarkers, and patients harboring these biomarkers may be predicted to be good candidates for treatment by the given drug.

As described above, additional modalities not illustrated in FIG. 2 may also be added to the heterogeneous network represented by a multi-modal statistical network trained in accordance with the techniques described herein. One such modality that may be added relates to patients. For example, patient information may be included in the heterogeneous network through proximity of their patients' properties (e.g., gene expression, mutation, copy number variation, DNA methylation) to other entities in the heterogeneous network, or by defining a patient entity as a new node in the heterogeneous network (e.g., with a single patient encoder and decoder used for projecting patient information to the common latent space).

In the former scenario, patients are represented in the multi-modal statistical model based on their gene expression profiles (or other experimentally procured attributes), and this information may be linked to other nodes (such as by proximity to known expression profiles of drugs and diseases), and the linked nodes may be used for projection into the latent space.

In the latter scenario, a new patient entity or node may be added to the heterogeneous network, with its own encoder and decoder included in the multi-modal statistical model. Network links in the heterogeneous network may be formed between individual patients (represented by a patient node) and the drug and disease nodes in the network, for example, based on patients known to react well to particular drugs or to harbor diseases. Furthermore, links in the heterogeneous network may be formed between two patients that harbor similar gene expression profiles or other experimentally procured biological information or attributes (e.g., DNA, RNA, Protein, medical imaging). The patient encoder and decoder may be trained in a similar manner as encoder/decoder pairs for other nodes in the heterogeneous network, as described above. Predictions using the trained patient encoder/decoder may be made, for example, between a patient of interest and a candidate drug, using one or more of the techniques described herein.

Figure 16:
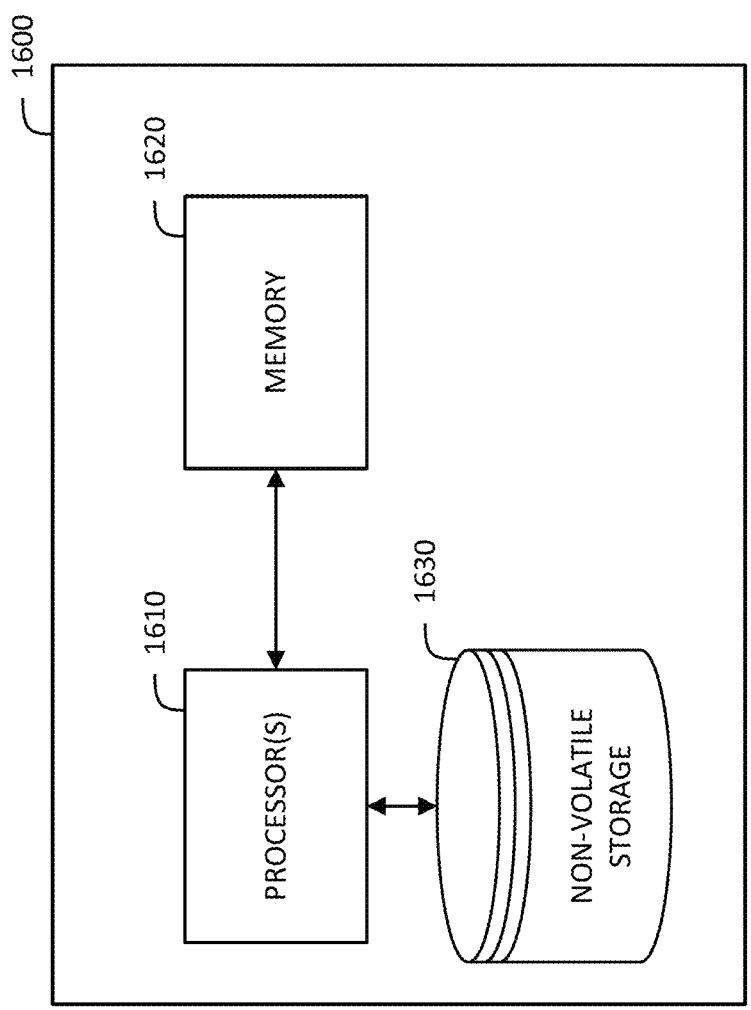
FIG. 16 shows components of an illustrative computer system on which some embodiments may be implemented.

An illustrative implementation of a computer system 1600 that may be used in connection with any of the embodiments of the disclosure provided herein is shown in FIG. 16. The computer system 1600 may include one or more computer hardware processors 1600 and one or more articles of manufacture that comprise non-transitory computer-readable storage media (e.g., memory 1620 and one or more non-volatile storage devices 1630). The processor 1610(s) may control writing data to and reading data from the memory 1620 and the non-volatile storage device(s) 1630 in any suitable manner. To perform any of the functionality described herein, the processor(s) 1610 may execute one or more processor-executable instructions stored in one or more non-transitory computer-readable storage media (e.g., the memory 1620), which may serve as non-transitory computer-readable storage media storing processor-executable instructions for execution by the processor(s) 1610.

The terms "program" or "software" are used herein in a generic sense to refer to any type of computer code or set of processor-executable instructions that can be employed to program a computer or other processor (physical or virtual) to implement various aspects of embodiments as discussed above. Additionally, according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, for example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term). The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A method for predicting a new disease indication for a given drug, the method comprising using at least one processor to perform:

training a statistical model by applying a self-supervised learning technique to training data to obtain a trained statistical model, the training data comprising representations of drugs in a first modality and representations of diseases in a second modality, the statistical model comprising a drug encoder, a disease encoder, a common representation space, a drug decoder and a disease decoder, wherein the training comprises:

projecting the representations of the drugs and diseases into the common representation space using the drug encoder to obtain drug vectors;

projecting the representations of the diseases into the common representation space using the disease encoder to obtain disease vectors;

combining the drug vectors with the disease vectors to obtain a plurality of joint drug-disease vectors;

providing the joint drug-disease vectors as input to the drug decoder and/or the disease decoder to obtain decoded output vectors;

determining a difference between the decoded output vectors, and at least some of the representations of drugs and diseases; and updating parameters of the statistical model based on the difference between the decoded output vectors and the at least some representations of drugs and diseases;

obtaining a representation of the given drug comprising data from the first modality;

obtaining representations of a plurality of diseases comprising data from the second modality; and predicting the new disease indication for the given drug using the trained statistical model, the trained statistical model comprising learned parameters for projecting data from the first and second modalities into the common representation space in which data from the first and second modalities can be compared, the learned parameters including parameters of the drug encoder trained to project drug representations into the common representation space and parameters of the disease encoder trained to project disease representations into the common representation space, the predicting comprising:

projecting the representation of the given drug into the common representation space using the learned parameters of the trained drug encoder to obtain a first vector in the common representation space representing the given drug;

projecting the representations of the plurality of diseases into the common representation space using the learned parameters of the trained disease encoder to obtain a plurality of vectors in the common representation space representing respective ones of the plurality of diseases;

determining a measure of similarity between the first vector representing the given drug and each of the plurality of vectors representing the plurality of diseases; and identifying at least one disease of the plurality of diseases as the new disease indication based on the measure of similarity between the first vector representing the given drug and each of the plurality of vectors representing the plurality of diseases.

2. The method of claim 1, wherein determining the measure of similarity between the first vector representing the given drug and the plurality of vectors representing comprises calculating a distance between the first vector representing the given drug and each of one or more of the plurality of vectors representing the plurality of diseases.

3. A computer system, comprising:
at least one computer processor; and
at least one storage device encoded with a plurality of instructions that, when executed by the at least one computer processor, performs a method of predicting a new disease indication for a given drug, the method comprising:
training a statistical model by applying a self-supervised learning technique to training data to obtain a trained statistical model, the training data comprising representations of drugs in a first modality and representations of diseases in a second modality, the statistical model comprising a drug encoder, a disease encoder, a common representation space, a drug decoder and a disease decoder, wherein the training comprises:
projecting the representations of the drugs and diseases into the common representation space using the drug encoder to obtain drug vectors;
projecting the representations of the diseases into the common representation space using the disease encoder to obtain disease vectors;
combining the drug vectors with the disease vectors to obtain a plurality of joint drug-disease vectors;
providing the joint drug-disease vectors as input to the drug decoder and/or the disease decoder to obtain decoded output vectors;
determining a difference between the decoded output vectors, and at least some of the representations of drugs and diseases; and
updating parameters of the statistical model based on the difference between the decoded output vectors and the at least some representations of drugs and diseases;
obtaining a representation of the given drug comprising data from the first modality;
obtaining representations of a plurality of diseases comprising data from the second modality; and
predicting the new disease indication for the given drug using the trained statistical model, the trained statistical model comprising learned parameters for projecting data from the first and second modalities into the common representation space in which data from the first and second modalities can be compared, the learned parameters including parameters of the drug encoder trained to project drug representations into the common representation space and parameters of the disease encoder trained to project disease representations into the common representation space, the predicting comprising:
projecting the representation of the given drug into the common representation space using the learned parameters of the trained drug encoder to obtain a first vector in the common representation space representing the given drug;
projecting the representations of the plurality of diseases into the common representation space using the learned parameters of the trained disease encoder to obtain a plurality of vectors in the common representation space representing respective ones of the plurality of diseases;
determining a measure of similarity between the first vector representing the given drug and each of the plurality of vectors representing the plurality of diseases; and
identifying at least one of the plurality of diseases as the new disease indication based on the measure of similarity between the first vector representing the given drug and the plurality of vectors representing the plurality of diseases.

4. The computer system of claim 3, wherein determining the measure of similarity between the first vector representing the given drug and the plurality of vectors representing the plurality of diseases comprises calculating a distance between the first vector representing the given drug and each of one or more of the plurality of diseases.

5. The method of claim 1, wherein:
the common representation space of the trained statistical model couples the trained drug encoder to the trained disease encoder.

6. The method of claim 1, wherein projecting the representation of the given drug into the common representation space using the learned parameters of the trained drug encoder further comprises:
providing as input to the trained drug encoder, the representation of the given drug to obtain the first vector in the common representation space representing the given drug.

7. The method of claim 1, wherein projecting the representations of the plurality of diseases into the common representation space using the trained disease encoder comprises:
providing as input to the trained disease encoder, the representations of the plurality of diseases to obtain the plurality of vectors in the common representation space.

8. The method of claim 1, wherein:
the training data further comprises information describing interactions between data elements in the representations of drugs in the first modality and data elements in the representations of diseases in the second modality; and
the training comprises training the statistical model using the information describing the interactions between the data elements in the representations of the drugs in the first modality and the data elements in the representations of the diseases in the second modality.

9. The method of claim 8, wherein the information describing interactions between the data elements in the representations of the drugs in the first modality and the data elements in the representations of the diseases in the second modality comprises information on drug-disease treatment.

10. The method of claim 1, wherein:
the first vector representing the given drug is a first N-dimensional vector;
the plurality of vectors representing the plurality of diseases are a plurality of N-dimensional vectors;
determining the measure of similarity between the first vector representing the given drug and the plurality of vectors representing the plurality of diseases comprises calculating distances between the first N-dimensional vector and each of the plurality of N-dimensional vectors; and
identifying at least one disease of the plurality of diseases as the new disease indication comprises identifying the at least one disease based on the calculated distances.

11. The method of claim 10, wherein predicting the new disease indication based on the calculated distances comprises selecting, as the predicted new disease indication, a disease associated with a respective one of the plurality of N-dimensional vectors having the shortest distance to the first N-dimensional vector in the common representation space.

12. The computer system of claim 3, wherein:
the common representation space of the trained statistical model couples the trained drug encoder to the trained disease encoder.

13. The computer system of claim 3, wherein projecting the representation of the given drug into the common representation space using the trained drug encoder further comprises:
providing as input to the trained drug encoder, the representation of the given drug to obtain the first vector in the common representation space representing the given drug.

14. The computer system of claim 12, wherein projecting the representations of the plurality of diseases into the common representation space using the learned parameters of the trained disease encoder comprises:
providing as input to the trained disease encoder, the representations of the plurality of diseases to obtain the plurality of vectors in the common representation space representing the plurality of diseases.

15. The computer system of claim 3, wherein:
the training data further comprises information describing interactions between data elements in the representations of drugs in the first modality and data elements in the representations of diseases in the second modality: and
the training comprises training the statistical model using the information describing the interactions between the data elements in the representations of the drugs in the first modality and the data elements in the representations of the diseases in the second modality.

16. The computer system of claim 15, wherein the information describing interactions between data elements in the drug training data and data elements in the disease training data comprises information on drug-disease treatment.

17. The computer system of claim 3, wherein:
the first vector representing the given drug is a first N-dimensional vector;
the plurality of vectors representing the plurality of diseases are a plurality of N-dimensional vectors;
determining the measure of similarity between the first vector representing the given drug and the plurality of vectors representing the plurality of diseases comprises calculating distances between the first N-dimensional vector and each of the plurality of N-dimensional vectors; and
identifying at least one disease of the plurality of diseases as the new disease indication comprises identifying the at least one disease based on the calculated distances.

18. The computer system of claim 17, wherein predicting the new disease indication based on the calculated distances comprises selecting, as the predicted new disease indication, a disease associated with a respective one of the plurality of N-dimensional vectors having the shortest distance to the first N-dimensional vector in the common representation space.

19. At least one non-transitory computer-readable storage medium storing instructions that, when executed by at least one computer processor, cause the at least one processor to perform a method of predicting a new disease indication for a given drug, the method comprising:
training a statistical model by applying a self-supervised learning technique to training data to obtain a trained statistical model, the training data comprising representations of drugs in a first modality and representations of diseases in a second modality, the statistical model comprising a drug encoder, a disease encoder, a common representation space, a drug decoder and a disease decoder, wherein the training comprises:
projecting the representations of the drugs and diseases into the common representation space using the drug encoder to obtain drug vectors;
projecting the representations of the diseases into the common representation space using the disease encoder to obtain disease vectors;
combining the drug vectors with the disease vectors to obtain a plurality of joint drug-disease vectors;
providing the joint drug-disease vectors as input to the drug decoder and/or the disease decoder to obtain decoded output vectors;
determining a difference between the decoded output vectors, and at least some of the representations of drugs and diseases; and
updating parameters of the statistical model based on the difference between the decoded output vectors and the at least some representations of drugs and diseases;
obtaining a representation of the given drug comprising data from the first modality;
obtaining representations of a plurality of diseases comprising data from the second modality; and
predicting the new disease indication for the given drug using the trained statistical model, the trained statistical model comprising learned parameters for projecting data from the first and second modalities into the common representation space in which data from the first and second modalities can be compared, the learned parameters including parameters of the drug encoder trained to project drug representations into the common representation space and parameters of the disease encoder trained to project disease representations into the common representation space, the predicting comprising:
projecting the representation of the given drug into the common representation space using the learned parameters of the trained drug encoder to obtain a first vector in the common representation space representing the given drug;
projecting the representations of the plurality of diseases into the common representation space using the learned parameters of the trained disease encoder to obtain a plurality of vectors in the common representation space representing respective ones of the plurality of diseases;

determining a measure of similarity between the first vector representing the given drug and each of the plurality of vectors representing the plurality of diseases; and identifying at least one of the plurality of diseases as the new disease indication based on the measure of similarity between the first vector representing the given drug and the plurality of vectors representing the plurality of diseases.

20. The at least one non-transitory computer-readable storage medium of claim 19, wherein:

the training data further comprises information describing interactions between data elements in the representations of drugs in the first modality and data elements in the representations of diseases in the second modality; and the training comprises training the statistical model using the information describing the interactions between the data elements in the representations of the drugs in the first modality and data elements in the representations of the diseases in the second modality.

* * * * *